(12) United States Patent
Tan et al.

(10) Patent No.: US 11,485,707 B2
(45) Date of Patent: Nov. 1, 2022

(54) DEUTERATED COMPOUNDS AS ROCK INHIBITORS

(71) Applicant: Fochon Pharmaceuticals, Ltd., Chongqing (CN)

(72) Inventors: Rui Tan, Chongqing (CN); Weipeng Zhang, Chongqing (CN); Yunling Wang, Chongqing (CN); Xingdong Zhao, Chongqing (CN); Tao Cheng, Chongqing (CN); Shu Lin, San Leandro, CA (US); Weibo Wang, Moraga, CA (US)

(73) Assignee: Fochon Pharmaceuticals, Ltd., Chongqing (CN)

( * ) Notice: Subject to any disclaimer, the term of this patent is extended or adjusted under 35 U.S.C. 154(b) by 146 days.

(21) Appl. No.: 17/040,577

(22) PCT Filed: Mar. 22, 2019

(86) PCT No.: PCT/CN2019/079326
§ 371 (c)(1),
(2) Date: Sep. 23, 2020

(87) PCT Pub. No.: WO2019/179525
PCT Pub. Date: Sep. 26, 2019

(65) Prior Publication Data
US 2021/0070711 A1 Mar. 11, 2021

Related U.S. Application Data

(60) Provisional application No. 62/711,375, filed on Jul. 27, 2018, provisional application No. 62/647,581, filed on Mar. 23, 2018.

(51) Int. Cl.
| | | |
|---|---|---|
| *A61K 31/472* | (2006.01) | |
| *C07D 217/00* | (2006.01) | |
| *A61P 27/06* | (2006.01) | |
| *C07D 217/02* | (2006.01) | |
| *A61P 27/02* | (2006.01) | |
| *A61K 45/06* | (2006.01) | |

(52) U.S. Cl.
CPC .......... *C07D 217/02* (2013.01); *A61K 31/472* (2013.01); *A61K 45/06* (2013.01); *A61P 27/02* (2018.01)

(58) Field of Classification Search
CPC ...... A61K 31/472; A61P 27/06; C07D 217/00
USPC .......................................... 514/310; 546/139
See application file for complete search history.

(56) References Cited

FOREIGN PATENT DOCUMENTS

| | | |
|---|---|---|
| EP | 3053913 A1 | 8/2016 |
| WO | 2006127587 A1 | 11/2006 |
| WO | 2007026920 A2 | 3/2007 |
| WO | 2014134388 A1 | 9/2014 |
| WO | 2017086941 A1 | 5/2017 |
| WO | 2017114275 A1 | 7/2017 |

OTHER PUBLICATIONS

International Search Report dated Jun. 26, 2019 in PCT/CN2019/079326.
Written Opinion dated Jun. 26, 2019 in PCT/CN2019/069326.
Extended European Search Report dated Nov. 19, 2021 in corresponding EP Application No. 19770464.6.
Sturdivant, Jill M., et al., "Discovery of the ROCK inhibitor netarsudil for the treatment of open-angle glaucoma," Bioorganic & Medicinal Chemistry Letters, vol. 26, pp. 2475-2480 (2016).
Foster, Allan B., "Deuterium Isotope Effects in the Metabolism of Drugs and Xenobiotics: Implications for Drug Design," Advances in Drug Research, vol. 14, pp. 1-40 (1985).
Kushner, D.J., et al., "Pharmacological uses and perspectives of heavy water and deuterated compounds," Can. J. Physiol. Pharmacol, vol. 77, pp. 79-88 (1999).

*Primary Examiner* — Raymond J Henley, III
(74) *Attorney, Agent, or Firm* — Ice Miller LLP

(57) ABSTRACT

Provided are compounds of Formula (I), or pharmaceutically acceptable salts thereof, pharmaceutical compositions comprising these compounds thereof, and use of these compounds in preparing drugs for inhibiting ROCK.

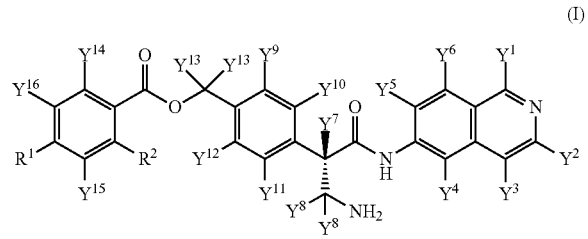

20 Claims, No Drawings

DEUTERATED COMPOUNDS AS ROCK INHIBITORS

CROSS-REFERENCE TO RELATED APPLICATION

This application is a Section 371 of International Application No. PCT/CN2019/079326 filed Mar. 22, 2019, which was published Sep. 26, 2019, under International Publication No. WO 2019/179525 A1, which claims priority under 35 U.S.C. § 119(b) to U.S. Patent Application No. 62/647,581 filed Mar. 23, 2018, and U.S. Patent Application No. 62/711,375 filed Jul. 27, 2018, the disclosures of which are incorporated herein by reference in their entireties.

FIELD OF THE INVENTION

Provided are certain compounds or pharmaceutically acceptable salts thereof which can inhibit enzymatic activity of Rho-associate kinase (ROCK) and may be useful for the treatment of diseases and disorders mediated by ROCK.

BACKGROUND OF THE INVENTION

Glaucoma, as an optic neuropathy, is one of the leading causes of irreversible blindness that affects more than 60.5 million individuals around the world, and is projected to affect nearly 80 million individuals by the year 2020. In glaucoma, progressive death of the retinal ganglion cells leads to optic nerve damage and, ultimately, visual field loss. Currently, it is widely accepted that increased intraocular pressure (IOP) is a main modifiable risk factor for glaucoma and lowering IOP is the only therapeutic intervention. In a healthy eye, aqueous humor (AH) outflows mainly through the trabecular meshwork TM to maintain IOP in the normal range. In a glaucomatous eye, elevated IOP arises in part as a consequence of impaired TM function, such as an increase in the contractile tone and stiffness of the TM, changes in extracellular matrix deposition, and changes in the permeability of the inner wall of Schlemm's canal.

New glaucoma therapeutics are urgently needed to efficiently target the diseased trabecular pathway. The inhibitors of Rho-associated kinase (ROCK) represent a new class of targeted therapies to treat glaucoma, such as the recently FDA-approved Rhopressa (netarsudil ophthalmic solution). ROCK encompass two isoforms, ROCK1 and ROCK2, which are serine/threonine kinases and downstream effectors of the small GTP-binding protein Rho. ROCK is widely expressed in various types of tissues including the TM. ROCK drives the assembly of actin stress fibers and focal adhesions, and pleiotropically regulates important cellular functions including cellular contraction, motility, morphology, polarity, cell division, and gene expression. The activation of Rho/ROCK signaling pathway in TM and Schlemm's canal cells causes actomyosin contraction, enhances extracellular matrix production and increases cell stiffness, resulting in the reduction of AH drainage and the elevation of IOP. Conversely, selective ROCK inhibitors can reduce the cell contraction and stiffness, and decrease the expression levels of fibrosis-related proteins, resulting in the relaxation of the TM, increase of the AH drainage and, eventually, the decrease of IOP.

Therefore, a compound having an inhibitory activity against ROCK will be successfully therapeutic approaches for patients with glaucoma. Although ROCK inhibitors were disclosed in the arts, there is a need for new ROCK inhibitors that have at least one advantageous property selected from potency, stability, selectivity, toxicity, pharmacodynamics properties and pharmacokinetics properties. In this regard, a novel class of ROCK inhibitors is provided herein.

DISCLOSURE OF THE INVENTION

Disclosed herein are certain novel deuterated compounds, pharmaceutically acceptable salts thereof, and pharmaceutical compositions thereof, and their use as pharmaceuticals.

In one aspect, disclosed herein is a compound of formula (I):

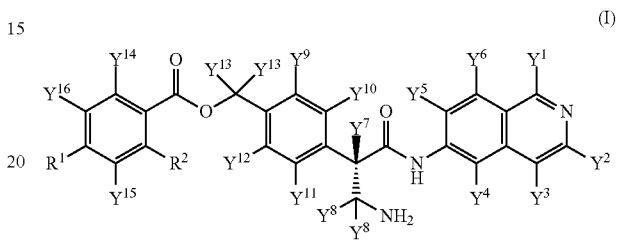

or a pharmaceutically acceptable salt thereof, wherein
$R^1$ is selected from $CH_3$, $CH_2D$, $CHD_2$ and $CD_3$;
$R^2$ is selected from $CH_3$, $CH_2D$, $CHD_2$ and $CD_3$;
$Y^1, Y^2, Y^3, Y^4, Y^5, Y^6, Y^7, Y^9, Y^{10}, Y^{11}, Y^{12}, Y^{14}, Y^{15}$ and $Y^{16}$ are each independently selected from hydrogen and deuterium;
each $Y^8$ is independently selected from hydrogen and deuterium, provided that both Y are the same;
each $Y^{13}$ is independently selected from hydrogen and deuterium, provided that both $Y^{13}$ are the same;
provided that the compound of formula (I) contains at least one deuterium atom.

In another aspect, disclosed herein is a pharmaceutical composition comprising a compound of formula (I) or a pharmaceutically acceptable salt thereof and a pharmaceutically acceptable excipient.

In yet another aspect, disclosed herein is a method for modulating ROCK, comprising administering to a system or a subject in need thereof, a therapeutically effective amount of a compound of formula (I) or a pharmaceutically acceptable salt thereof or pharmaceutical compositions thereof, thereby modulating said ROCK.

In yet another aspect, disclosed is a method to treat, ameliorate or prevent a condition which responds to inhibition of ROCK comprising administering to a system or subject in need of such treatment an effective amount of a compound of formula (I) or a pharmaceutically acceptable salt thereof or pharmaceutical compositions thereof, and optionally in combination with a second therapeutic agent, thereby treating said condition.

Alternatively, disclosed herein is the use of a compound of formula (I) or a pharmaceutically acceptable salt thereof in the manufacture of a medicament for treating a condition mediated by ROCK. In particular embodiments, the compounds of the disclosure may be used alone or in combination with a second therapeutic agent to treat a condition mediated by ROCK.

Alternatively, disclosed is a compound of formula (I) or a pharmaceutically acceptable salt for treating a condition mediated by ROCK.

Specifically, the condition herein includes but not limited to, eye disorders such as glaucoma, ocular hypertension or a neurodegenerative eye disease.

Furthermore, the disclosure provides methods for treating elevated intraocular pressure, comprising administering to a system or subject in need of such treatment an effective amount of a compound of formula (I) or a pharmaceutically acceptable salt thereof or pharmaceutical compositions thereof, and optionally in combination with a second therapeutic agent, thereby treating said condition.

Alternatively, the present disclosure provides the use of a compound of formula (I) or a pharmaceutically acceptable salt thereof in the manufacture of a medicament for treating elevated intraocular pressure. In particular examples, the compounds of the disclosure may be used alone or in combination with a chemotherapeutic agent to treat eye disorders.

Specifically, the eye disorder disclosed herein includes but not limited to, glaucoma, ocular hypertension and a neurodegenerative eye disease.

In the above methods for using the compounds of the disclosure, a compound of formula (I) or a pharmaceutically acceptable salt thereof may be administered to a system comprising cells or tissues, or to a subject including a mammalian subject such as a human or animal subject.

Certain Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, $CH_2O$ is equivalent to $OCH_2$.

As used herein, the term "optionally substituted" means unsubstituted or substituted. The term "substituted" means that a hydrogen atom is removed and replaced by a substituent. It is to be understood that substitution at a given atom is limited by valency. Throughout the definitions, the term "$C_{i-j}$" indicates a range which includes the endpoints, wherein i and j are integers and indicate the number of carbons. Examples include $C_{1-4}$, $C_{1-10}$, $C_{3-10}$, and the like.

The term "deuterium" or "D" refers to an isotope of hydrogen whose nucleus contains one proton and one neutron. When a particular position is designated as having deuterium, it is understood that the abundance of deuterium at that position is greater than the natural abundance of deuterium.

The term "substituted with deuterium" refers to the replacement of one or more hydrogen atoms with a corresponding number of deuterium atoms.

The term "alkyl", employed alone or in combination with other terms, refers to both branched and straight-chain saturated aliphatic hydrocarbon groups having the specified number of carbon atoms. Unless otherwise specified, "alkyl" refers to $C_{1-10}$ alkyl. For example, $C_{1-6}$, as in "$C_{1-6}$ alkyl" is defined to include groups having 1, 2, 3, 4, 5, or 6 carbons in a linear or branched arrangement. For example, "$C_{1-8}$ alkyl" includes but is not limited to methyl, ethyl, n-propyl, i-propyl, n-butyl, t-butyl, i-butyl, pentyl, hexyl, heptyl, and octyl.

The term "cycloalkyl", employed alone or in combination with other terms, refers to a monocyclic or bridged hydrocarbon ring system. The monocyclic cycloalkyl is a carbocyclic ring system containing three to ten carbon atoms, zero heteroatoms and zero double bonds. Examples of monocyclic ring systems include cyclopropyl, cyclobutyl, cyclopentyl, cyclohexyl, cycloheptyl, and cyclooctyl. The monocyclic ring may contain one or two alkylene bridges, each consisting of one, two, or three carbon atoms, each linking two non-adjacent carbon atoms of the ring system. Representative examples of such bridged cycloalkyl ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.03,7]nonane, and tricyclo[3.3.1.13,7]decane (adamantane). The monocyclic and bridged cycloalkyl can be attached to the parent molecular moiety through any substitutable atom contained within the ring system.

The term "halogen" (or "halo") refers to fluorine, chlorine, bromine and iodine.

The term "alkoxy", employed alone or in combination with other terms, refers to an alkyl radical that is single bonded to an oxygen atom. The attachment point of an alkoxy radical to a molecule is through the oxygen atom. An alkoxy radical may be depicted as —O-alkyl. The term "$C_{1-10}$ alkoxy" refers to an alkoxy radical containing from one to ten carbon atoms, having straight or branched moieties. Alkoxy groups, includes but is not limited to, methoxy, ethoxy, propoxy, isopropoxy, butoxy, hexyloxy, and the like.

The term "cycloalkoxy", employed alone or in combination with other terms, refers to cycloalkyl radical that is single bonded to an oxygen atom. The attachment point of a cycloalkoxy radical to a molecule is through the oxygen atom. A cycloalkoxy radical may be depicted as —O-cycloalkyl. "$C_{3-10}$ cycloalkoxy" refers to a cycloalkoxy radical containing from three to ten carbon atoms. Cycloalkoxy groups, includes but is not limited to, cyclopropoxy, cyclobutoxy, cyclohexyloxy, and the like.

The term "pharmaceutically acceptable salts" refers to salts prepared from pharmaceutically acceptable non-toxic bases or acids including inorganic or organic bases and inorganic or organic acids. Salts derived from inorganic bases may be selected, for example, from aluminum, ammonium, calcium, copper, ferric, ferrous, lithium, magnesium, manganic, manganous, potassium, sodium, and zinc salts. Further, for example, the pharmaceutically acceptable salts derived from inorganic bases may be selected from ammonium, calcium, magnesium, potassium, and sodium salts. Salts in the solid form may exist in one or more crystal structures, and may also be in the form of hydrates. Salts derived from pharmaceutically acceptable organic non-toxic bases may be selected, for example, from salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, and tripropylamine, tromethamine.

When the compound disclosed herein is basic, salts may be prepared using at least one pharmaceutically acceptable non-toxic acid, selected from inorganic and organic acids. Such acid may be selected, for example, from acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids. In some embodiments, such acid may be selected, for example, from citric, hydrobromic, hydrochloric, maleic, phosphoric, sulfuric, fumaric, and tartaric acids.

The terms "administration of" and or "administering" a compound or a pharmaceutically acceptable salt should be understood to mean providing a compound or a pharmaceutically acceptable salt thereof to the individual in recognized need of treatment.

The term "effective amount" means the amount of the a compound or a pharmaceutically acceptable salt that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to a pharmaceutical composition is intended to encompass a product comprising the active ingredient (s), and the inert ingredient (s) that make up the carrier, as well as any product which results, directly or indirectly, from combination, complexation or aggregation of any two or more of the ingredients, or from dissociation of one or more of the ingredients, or from other types of reactions or interactions of one or more of the ingredients.

The term "pharmaceutically acceptable" it is meant compatible with the other ingredients of the formulation and not unacceptably deleterious to the recipient thereof.

The term "subject" as used herein in reference to individuals suffering from a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The term "protecting group" or "Pg" refers to a substituent that can be commonly employed to block or protect a certain functionality while reacting other functional groups on the compound. For example, an "amino-protecting group" is a substituent attached to an amino group that blocks or protects the amino functionality in the compound. Suitable amino-protecting groups include but are not limited to acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include but are not limited to acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The term "NH protecting group" as used herein includes, but not limited to, trichloroethoxycarbonyl, tribromoethoxycarbonyl, benzyloxycarbonyl, para-nitrobenzlcarbonyl, ortho-bromobenzyloxycarbonyl, chloroacetyl, dichloroacetyl, trichloroacetyl, trifluoroacetyl, phenylacetyl, formyl, acetyl, benzoyl, tert-amyloxycarbonyl, tert-butoxycarbonyl, para-methoxybenzyloxycarbonyl, 3,4-dimethoxybenzyloxycarbonyl, 4-(phenylazo)-benzyloxycarbonyl, 2-furfuryloxycarbonyl, diphenylmethoxycarbonyl, 1,1-dimethylpropoxycarbonyl, isopropoxycarbonyl, phthaloyl, succinyl, alanyl, leucyl, 1-adamantyloxycarbonyl, 8-quinolyloxycarbonyl, benzyl, diphenylmethyl, triphenylmethyl, 2-nitrophenylthio, methanesulfonyl, para-toluenesulfonyl, N,N-dimethylaminomethylene, benzylidene, 2-hydroxybenzylidene, 2-hydroxy-5-chlorobenzylidene, 2-hydroxy-1-naphthylmethylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclo-hexylidene, diphenylphosphoryl, dibenzylphosphoryl, 5-methyl-2-oxo-2H-1,3-dioxol-4-yl-methyl, trimethylsilyl, triethylsilyl, and triphenylsilyl.

The term "C(O)OH protecting group" as used herein includes, but not limited to, methyl, ethyl, n-propyl, isopropyl, 1,1-dimethylpropyl, n-butyl, tert-butyl, phenyl, naphthyl, benzyl, diphenylmethyl, triphenylmethyl, para-nitrobenzyl, para-methoxybenzyl, bis(para-methoxyphenyl)methyl, acetylmethyl, benzoylmethyl, para-nitrobenzoylmethyl, para-bromobenzoylmethyl, para-methanesulfonylbenzoylmethyl, 2-tetrahydropyranyl, 2-tetrahydrofuranyl, 2,2,2-trichloro-ethyl, 2-(trimethylsilyl)ethyl, acetoxymethyl, propionyloxymethyl, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl)ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

The term "OH or SH protecting group" as used herein includes, but not limited to, benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethylsilylethyl, 1,1-dimethyl-2-propenyl, 3-methyl-3-butenyl, allyl, benzyl (phenylmethyl), para-methoxybenzyl, 3,4-dimethoxybenzyl, diphenylmethyl, triphenylmethyl, tetrahydrofuryl, tetrahydropyranyl, tetrahydrothiopyranyl, methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are designated as being of cis or trans configuration. Furthermore, the invention contemplates the various isomers and mixtures thereof resulting from the disposal of substituents around an adamantane ring system. Two substituents around a single ring within an adamantane ring system are designated as being of Z or E relative configuration. For examples, see C. D. Jones, M. Kaselj, R. N. Salvatore, W. J. le Noble J. Org. Chem. 1998, 63, 2758-2760.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85-90%, more preferably an excess of about 95-99%, and still more preferably an excess greater than about 99%. Accordingly, this invention includes racemic mixtures, relative and absolute stereoisomers, and mixtures of relative and absolute stereoisomers.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, nitrogen, oxygen, phosphorous, sulfur, fluorine, chlorine, and iodine include, but are not limited to, $^{2}H$, $^{3}H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^{2}H$), tritium ($^{3}H$) or $^{14}C$ isotopes. Therefore when a substituent is described as hydrogen, it also incorporates the isotopic equivalents such as deuterium and tritium, in particular deuterium (D). Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuterated acid such as $D_2SO_4/D_2O$. In addition to the above, relevant procedures and intermediates are disclosed, for instance, in Lizondo, J et al, Drugs Fut, 21(11), 1116 (1996); Brickner, S J et al., J Med Chem, 39(3), 673 (1996); Mallesham, B et al, Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338;

20090105307; 20090105147; 20090093422; 20090088416; and 20090082471, the methods are hereby incorporated by reference.

The isotope-labeled compounds of the invention may be used as standards to determine the effectiveness of STAT3 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al, J. Labelled Comp. Radiopharmaceut., 36(10):927-932 (1995); Kushner et al., Can. J. Physiol. Pharmacol, 77, 79-88 (1999)).

In addition, non-radioactive isotope containing drugs, such as deuterated drugs called "heavy drugs" can be used for the treatment of diseases and conditions related to STAT3 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

In an embodiment, the invention provides a compound selected from

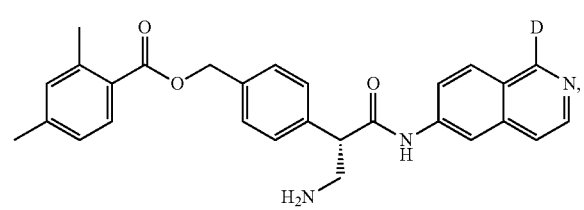

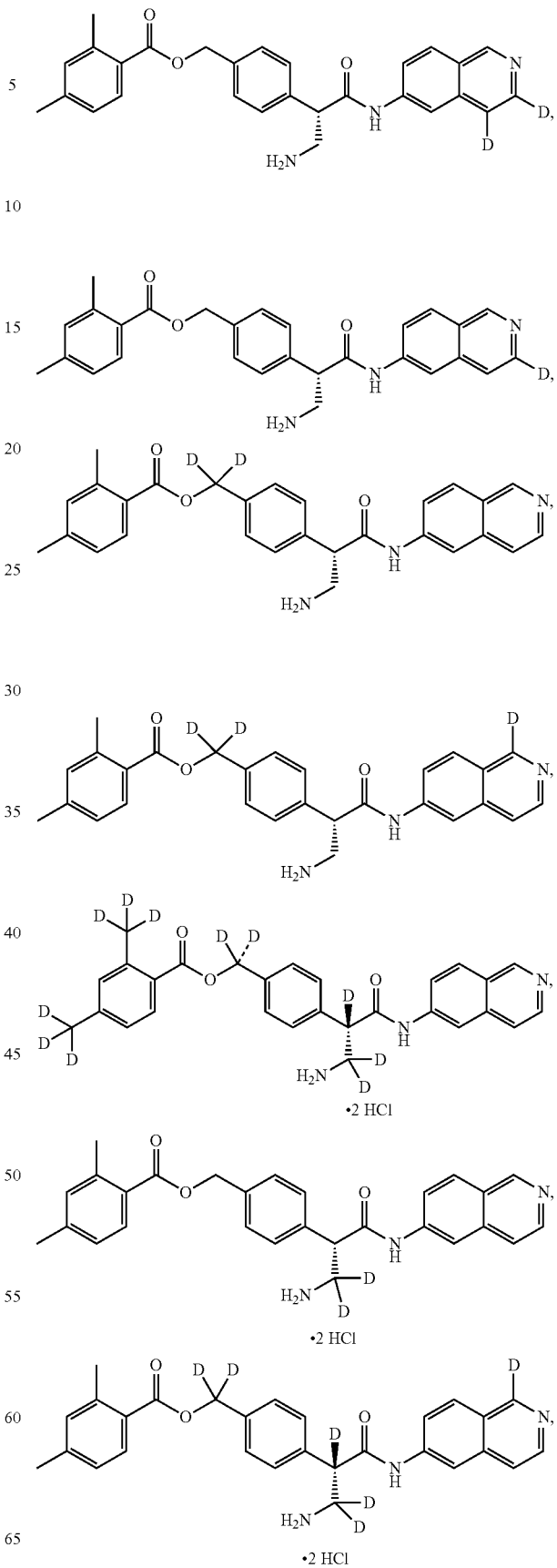

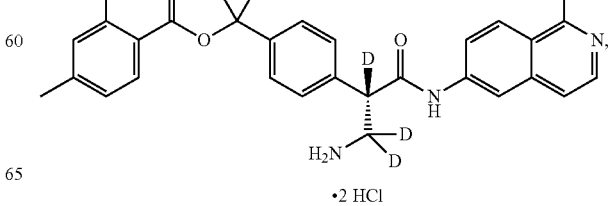

11
-continued
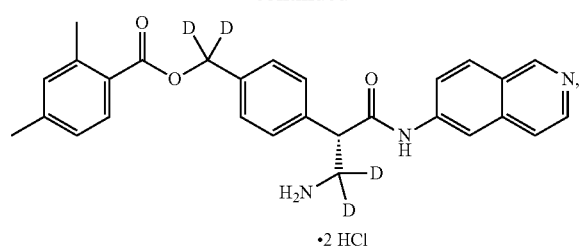
•2 HCl
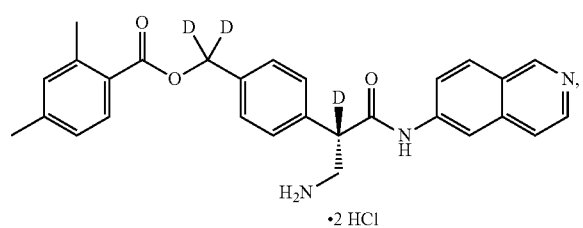
•2 HCl
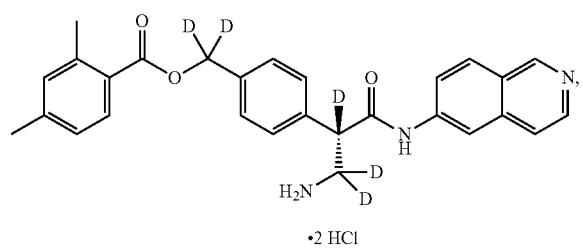
•2 HCl
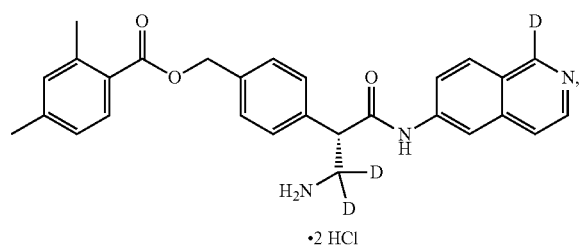
•2 HCl
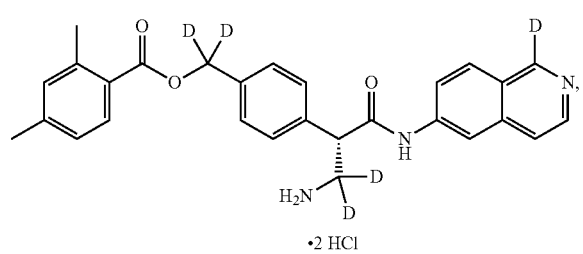
•2 HCl
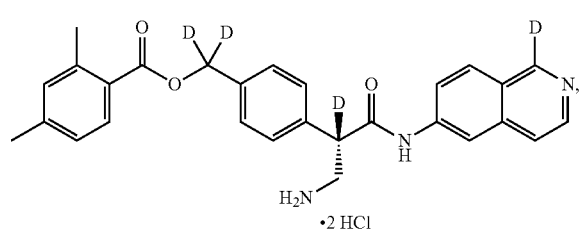
•2 HCl
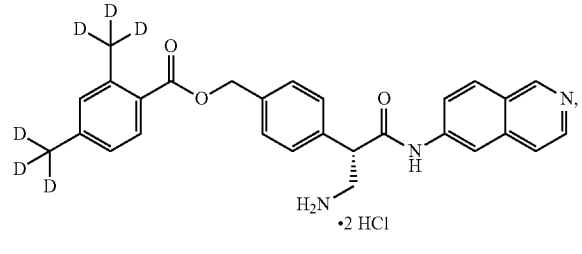
•2 HCl
12
-continued
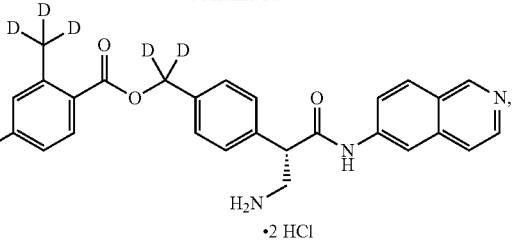
•2 HCl
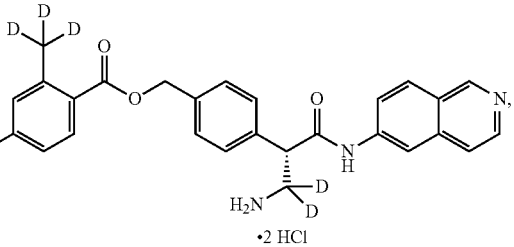
•2 HCl
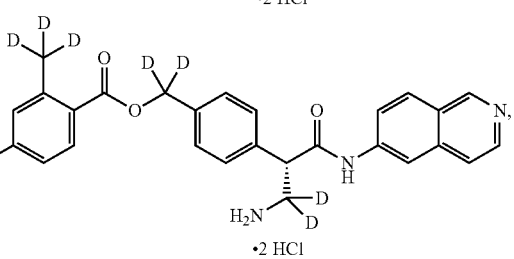
•2 HCl
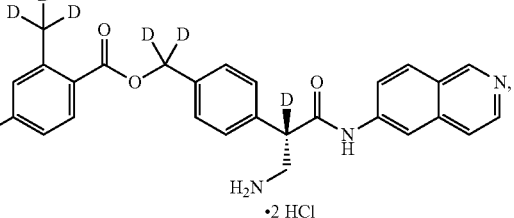
•2 HCl
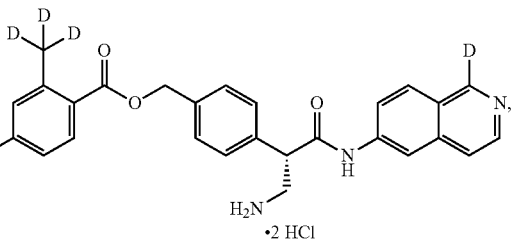
•2 HCl
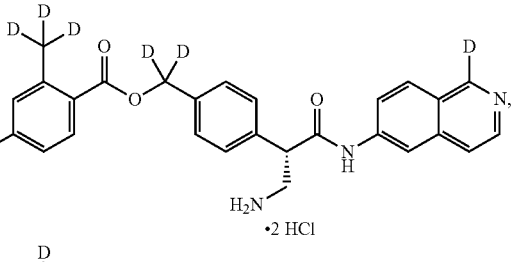
•2 HCl
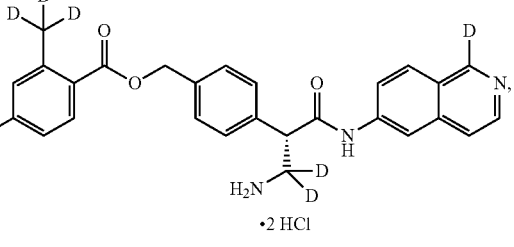
•2 HCl -continued

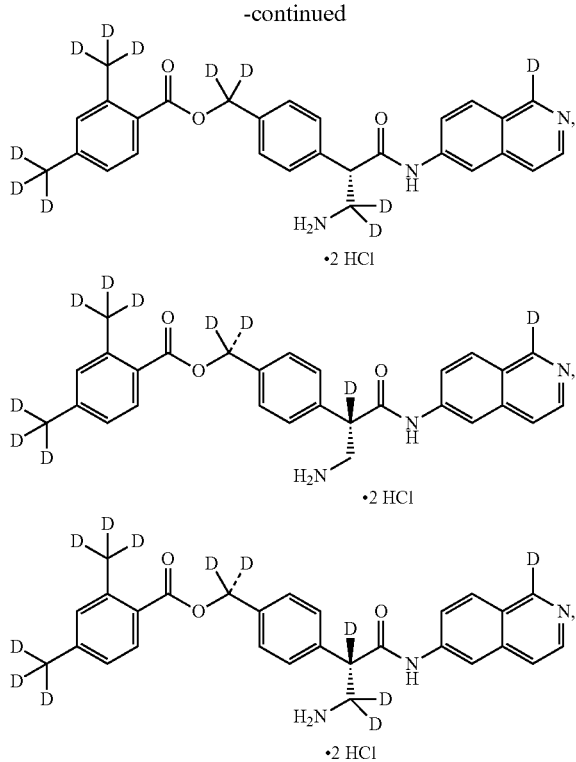

and pharmaceutically acceptable salts thereof.

In an Embodiment (1), this invention provides a compound of formula (I)

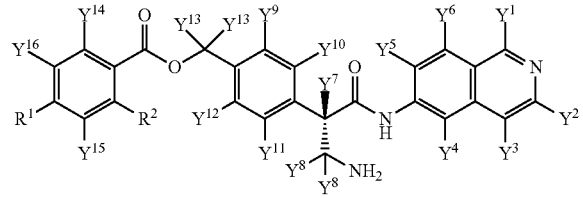

or a pharmaceutically acceptable salt thereof, wherein
$R^1$ is selected from $CH_3$, $CH_2D$, $CHD_2$ and $CD_3$;
$R^2$ is selected from $CH_3$, $CH_2D$, $CHD_2$ and $CD_3$;
$Y^1, Y^2, Y^3, Y^4, Y^5, Y^6, Y^7, Y^9, Y^{10}, Y^{11}, Y^{12}, Y^{14}, Y^{15}$ and $Y^{16}$ are each independently selected from hydrogen and deuterium;
each $Y^8$ is independently selected from hydrogen and deuterium, provided that both $Y^8$ are the same;
each $Y^{13}$ is independently selected from hydrogen and deuterium, provided that both $Y^{13}$ are the same;
provided that the compound of formula (I) contains at least one deuterium atom.

In another Embodiment (2), the invention provides a compound of Embodiment (1) or a pharmaceutically acceptable salt thereof, wherein $Y^1$ is deuterium.

In another Embodiment (3), the invention provides a compound of any one of Embodiment (1)-(2) or a pharmaceutically acceptable salt thereof, wherein $Y^2$ is deuterium.

In another Embodiment (4), the invention provides a compound of any one of Embodiment (1)-(3) or a pharmaceutically acceptable salt thereof, wherein $Y^3$ is deuterium.

In another Embodiment (5), the invention provides a compound of any one of Embodiment (1)-(4) or a pharmaceutically acceptable salt thereof, wherein $Y^7$ is deuterium.

In another Embodiment (6), the invention provides a compound of any one of Embodiment (1)-(5) or a pharmaceutically acceptable salt thereof, wherein both $Y^8$ are deuterium.

another Embodiment (7), the invention provides a compound of any one of Embodiment (1)-(6) or a pharmaceutically acceptable salt thereof, wherein both $Y^{13}$ are deuterium.

In another Embodiment (8), the invention provides a compound of any one of Embodiment (1)-(7) or a pharmaceutically acceptable salt thereof, wherein $R^1$ is selected from $CH_3$ and $CD_3$.

In another Embodiment (9), the invention provides a compound of any one of Embodiment (1)-(8) or a pharmaceutically acceptable salt thereof, wherein $R^2$ is selected from $CH_3$ and $CD_3$.

In another Embodiment (10), the invention provides a compound selected from

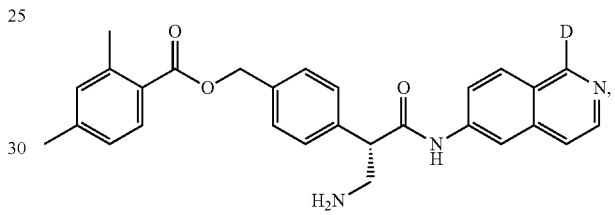

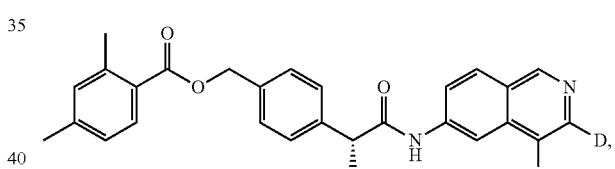

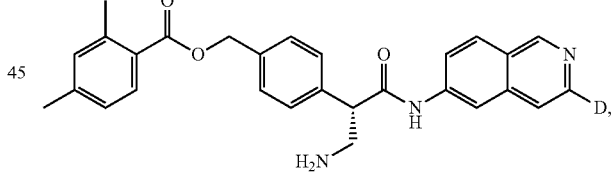

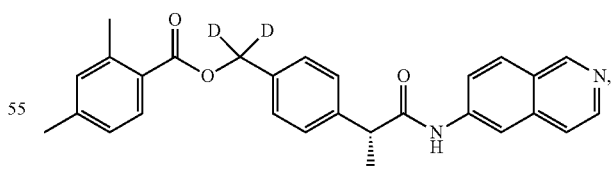

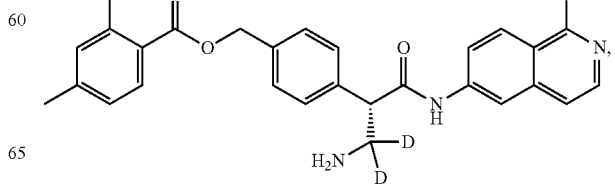

15
-continued
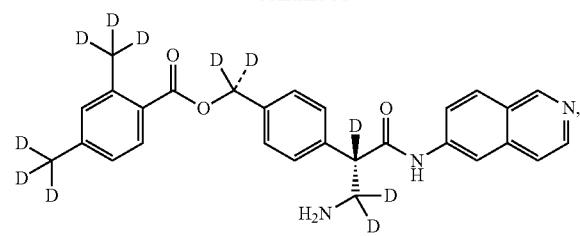
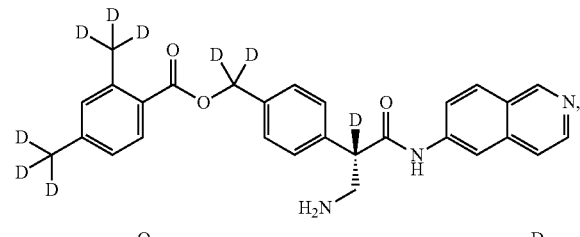
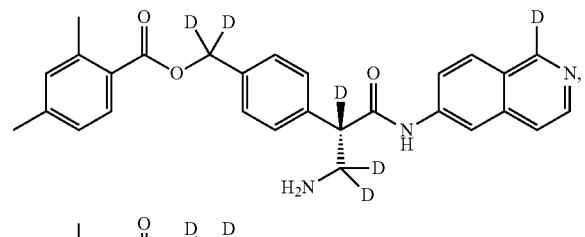
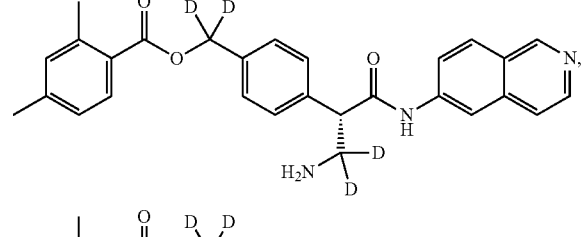
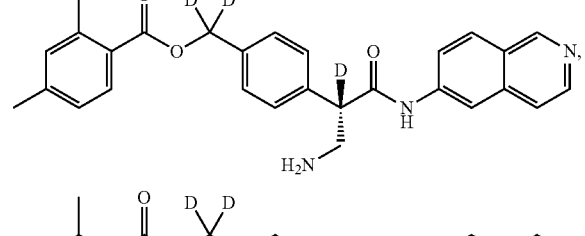
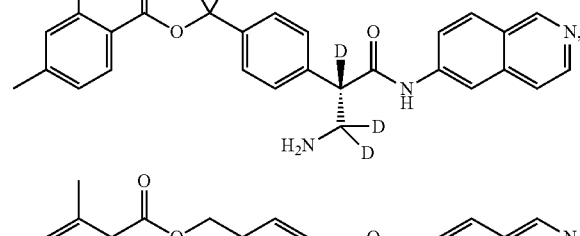
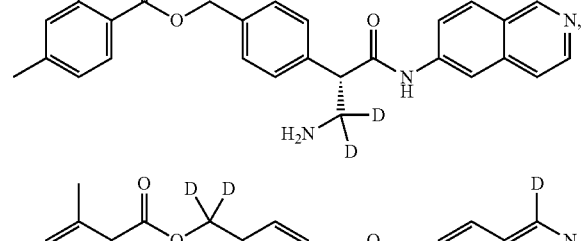
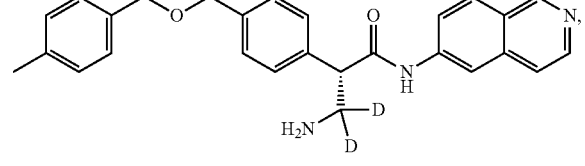
16
-continued
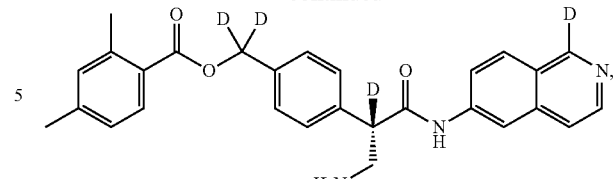
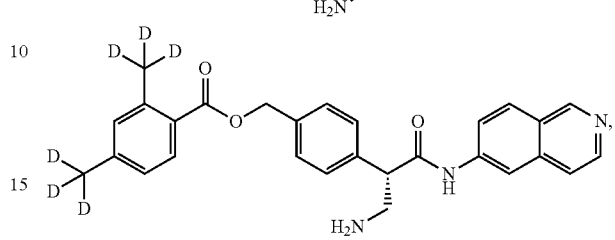
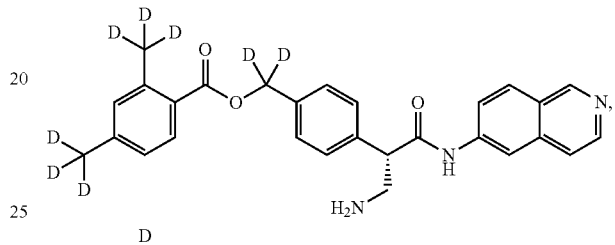
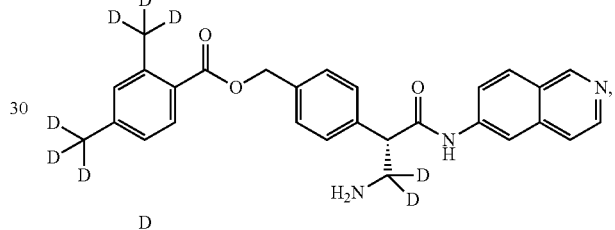
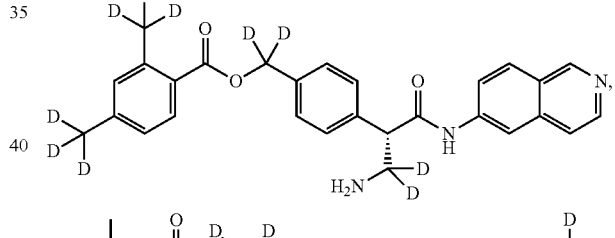
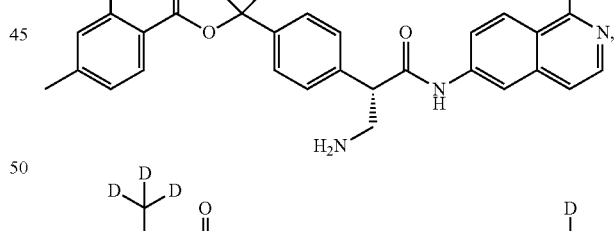
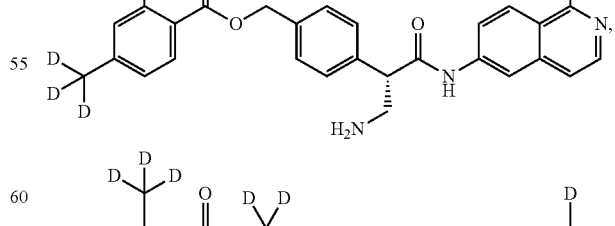
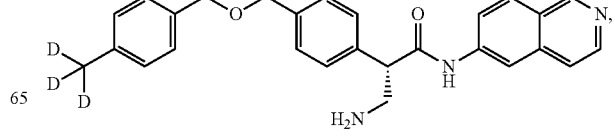

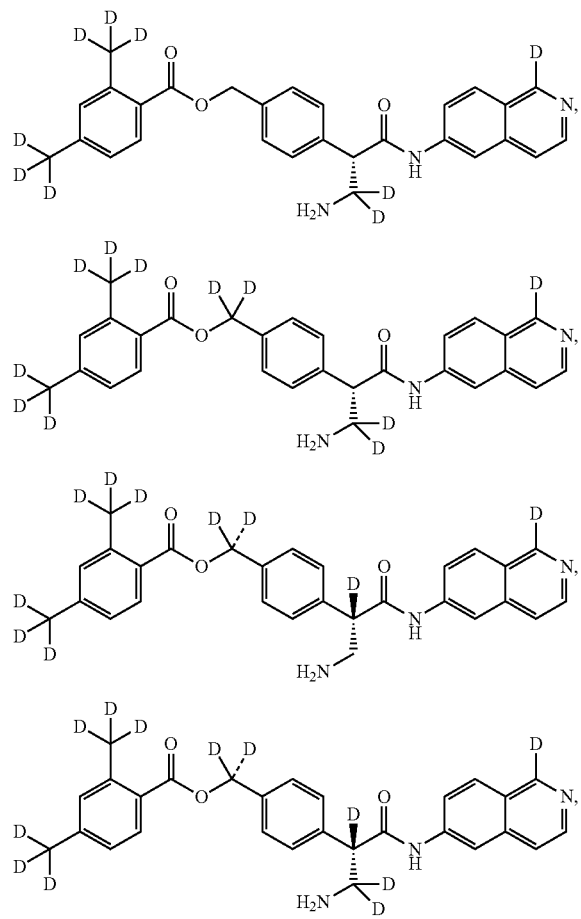
and pharmaceutically acceptable salts thereof.
In another Embodiment (11), the invention provides a compound of Embodiment (10) or a pharmaceutically acceptable salt thereof, a compound selected from
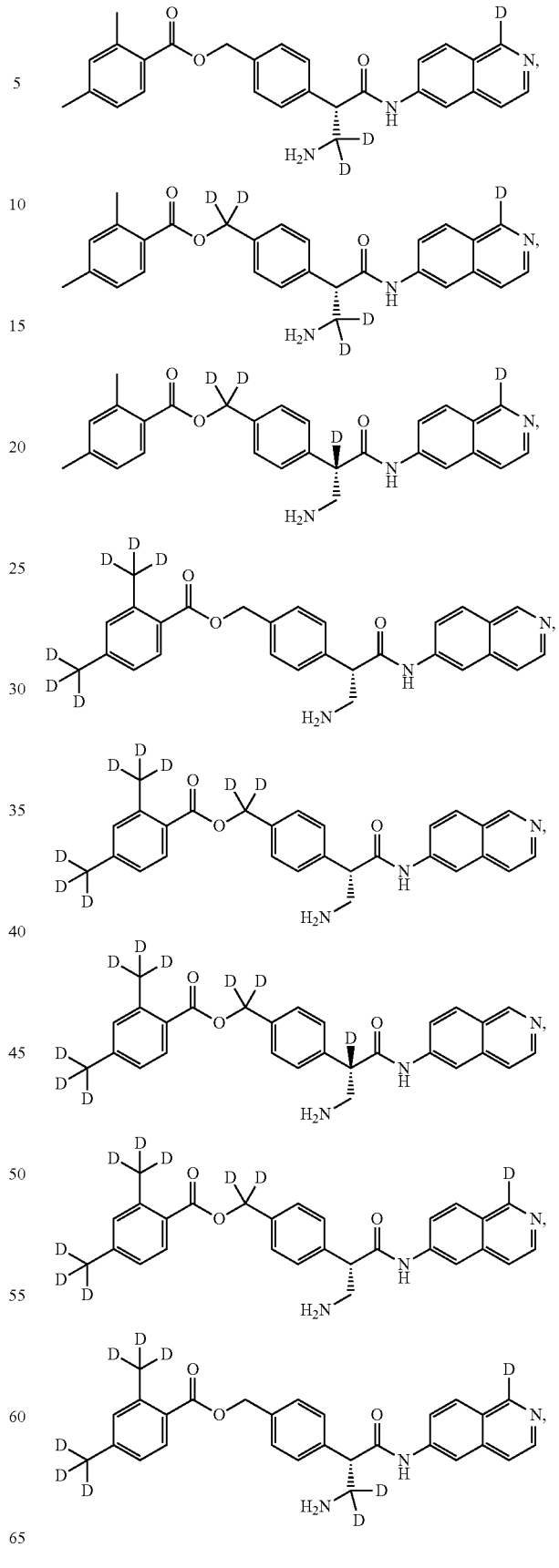
and pharmaceutically acceptable salts thereof.

In another Embodiment (12), the invention provides a compound of Embodiment (11) or a pharmaceutically acceptable salt thereof, a compound selected from

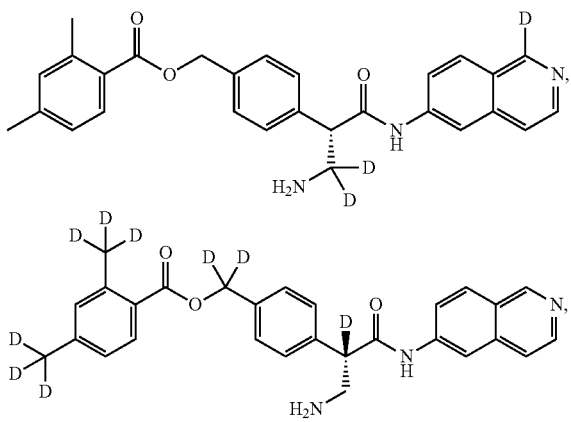

and pharmaceutically acceptable salts thereof.

In another Embodiment (13), the invention provides a compound of any one of Embodiment (1)-(12) or a pharmaceutically acceptable salt thereof, wherein the pharmaceutically acceptable salt thereof is hydrochloride.

In another Embodiment (14), the invention provides a compound of Embodiment (13) or a pharmaceutically acceptable salt thereof, wherein the pharmaceutically acceptable salt thereof is dihydrochloride.

In another Embodiment (15), the invention provides a compound of Embodiment (14) or a pharmaceutically acceptable salt thereof, wherein the pharmaceutically acceptable salt thereof selected from

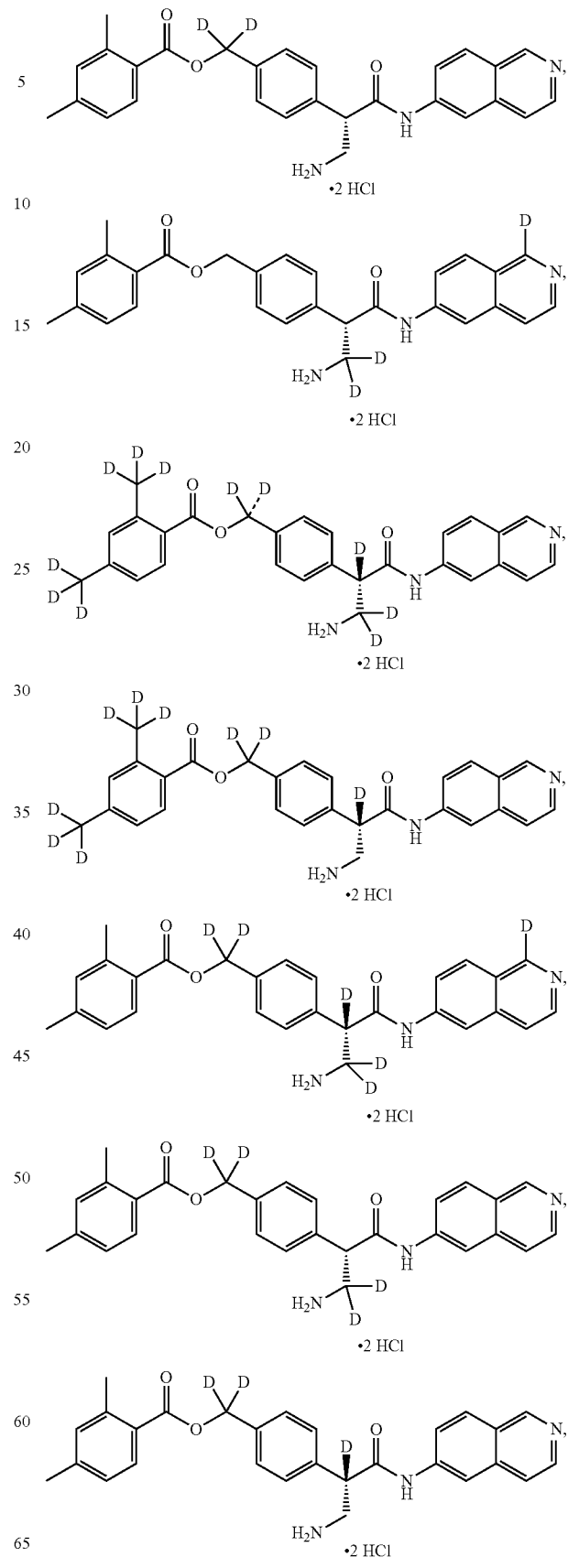

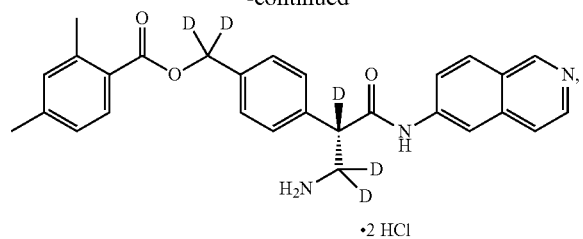
•2 HCl
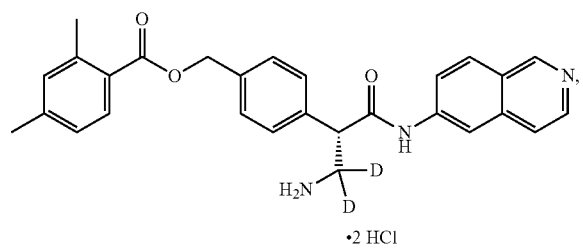
•2 HCl
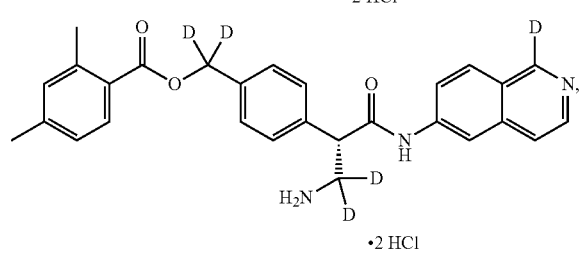
•2 HCl
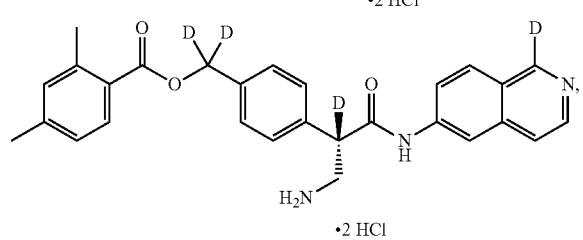
•2 HCl
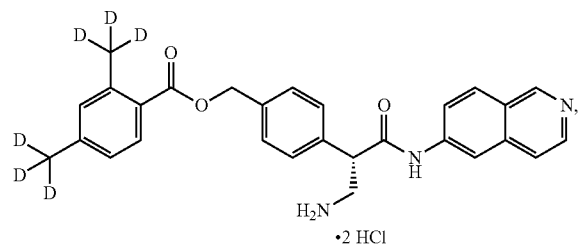
•2 HCl
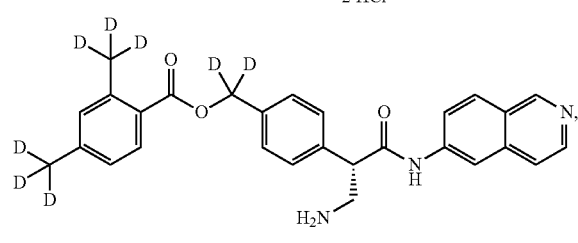
•2 HCl
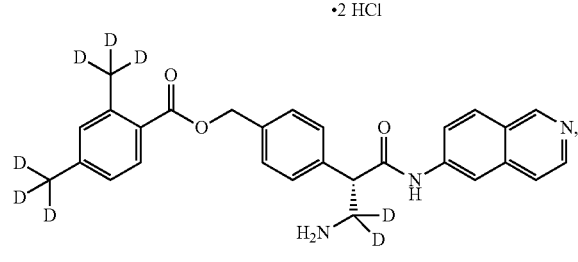
•2 HCl
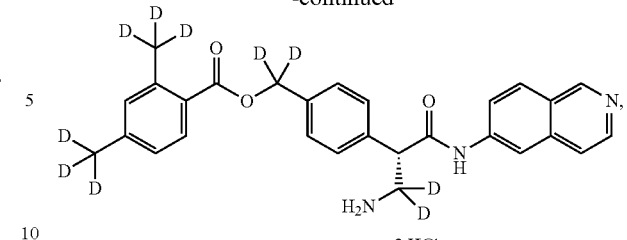
•2 HCl
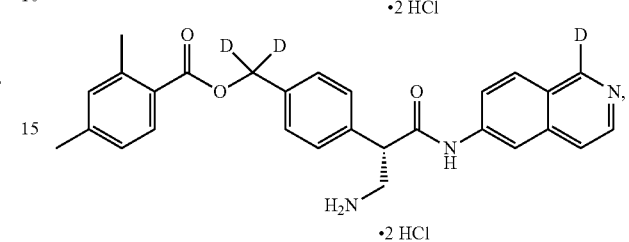
•2 HCl
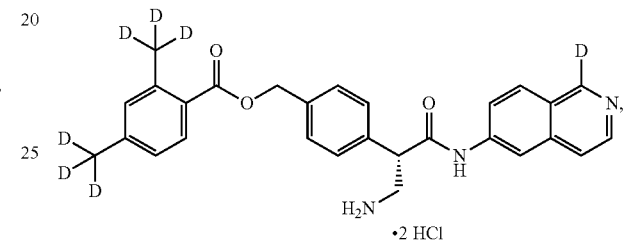
•2 HCl
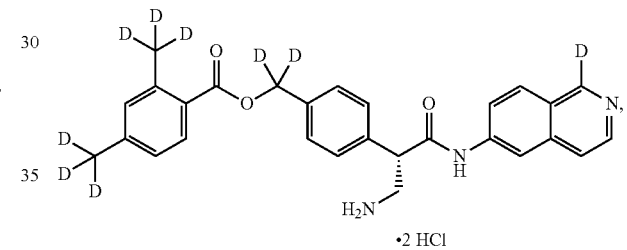
•2 HCl
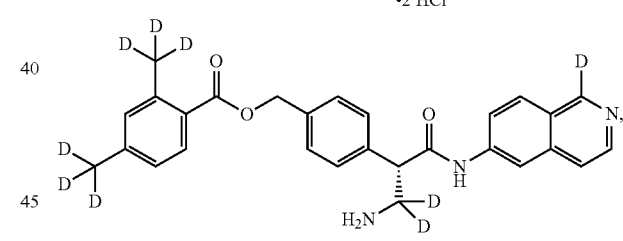
•2 HCl
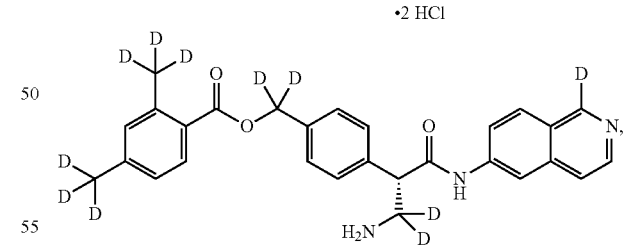
•2 HCl
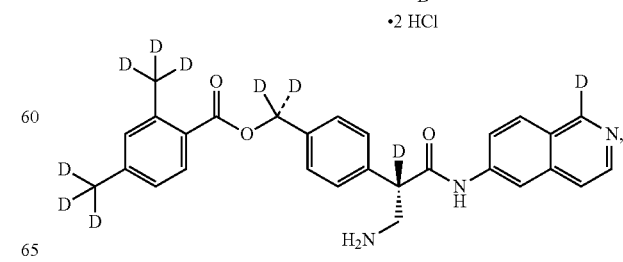
•2 HCl -continued

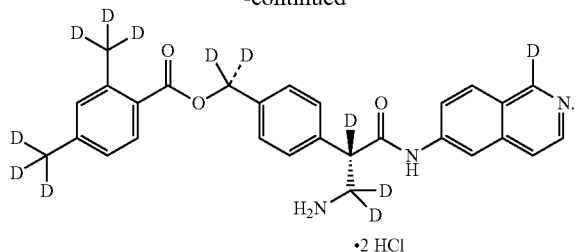

·2 HCl

In another Embodiment (16), the invention provides a pharmaceutical composition comprising a compound of any one of Embodiments (1) to (15) or a pharmaceutically acceptable salt thereof and at least one pharmaceutically acceptable carrier.

In another Embodiment (17), the invention provides a method of treating, ameliorating or preventing a condition, which responds to inhibition of ROCK, comprising administering to a subject in need of such treatment an effective amount of a compound of any one of Embodiments (1) to (15), or a pharmaceutically acceptable salt thereof, or a pharmaceutical composition thereof, and optionally in combination with a second therapeutic agent.

In another Embodiment (18), the invention provides a use of a compound of any one of Embodiments (1) to (16) or a pharmaceutically acceptable salt thereof in the preparation of a medicament for treating elevated intraocular pressure.

In yet another of its aspects, there is provided a kit comprising a compound disclosed herein, or a pharmaceutically acceptable salt thereof; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound disclosed herein, or a pharmaceutically acceptable salt thereof; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, there is provided a therapeutic method comprising administering a compound disclosed herein, or a pharmaceutically acceptable salt thereof.

In another of its aspects, there is provided a method of inhibiting ROCK comprising contacting the ROCK with a compound disclosed herein, or a pharmaceutically acceptable salt thereof.

In yet another of its aspects, there is provided a method of inhibiting ROCK comprising causing a compound disclosed herein, or a pharmaceutically acceptable salt thereof to be present in a subject in order to inhibit the ROCK in vivo.

In a further of its aspects, there is provided a method of inhibiting ROCK comprising administering a first compound to a subject that is converted in vivo to a second compound wherein the second compound inhibits the ROCK in vivo, the second compound being a compound according to any one of the above embodiments and variations.

In another of its aspects, there is provided a method of treating a disease state for which ROCK possesses activity that contributes to the pathology and/or symptomology of the disease state, the method comprising causing a compound disclosed herein, or a pharmaceutically acceptable salt thereof to be present in a subject in a therapeutically effective amount for the disease state.

In a further of its aspects, there is provided a method of treating a disease state for which ROCK possesses activity that contributes to the pathology and/or symptomology of the disease state, the method comprising administering a first compound to a subject that is converted in vivo to a second compound wherein the second compound inhibits the ROCK in vivo. It is noted that the compounds of the present invention may be the first or second compounds.

In one variation of each of the above methods the disease state is selected from the eye disorders such as glaucoma, ocular hypertension or a neurodegenerative eye disease.

In another of its aspects, there is provided a method of treating a disease state for which a mutation in the ROCK gene contributes to the pathology and/or symptomology of the disease state including, for example, glaucoma, ocular hypertension or a neurodegenerative eye disease.

In still another of its aspects, the present invention relates to the use of a compound of any of the above embodiments and variations as a medicament. In yet another of its aspects, the present invention relates to the use of a compound according to any one of the above embodiments and variations in the manufacture of a medicament for inhibiting ROCK.

In a further of its aspects, the present invention relates to the use of a compound according to any one of the above embodiments and variations in the manufacture of a medicament for treating a disease state for which ROCK possesses activity that contributes to the pathology and/or symptomology of the disease state.

Administration and Pharmaceutical Compositions

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors known to those of ordinary skill in the art. For example, for the treatment of neoplastic diseases and immune system disorders, the required dosage will also vary depending on the mode of administration, the particular condition to be treated and the effect desired.

In general, satisfactory results are indicated to be obtained systemically at daily dosages of from about 0.001 to about 100 mg/kg per body weight, or particularly, from about 0.03 to 2.5 mg/kg per body weight. An indicated daily dosage in the larger mammal, e.g. humans, may be in the range from about 0.5 mg to about 2000 mg, or more particularly, from about 0.5 mg to about 1000 mg, conveniently administered, for example, in divided doses up to four times a day or in retard form. Suitable unit dosage forms for oral administration comprise from ca. 1 to 50 mg active ingredient.

Compounds of the disclosure may be administered as pharmaceutical compositions by any conventional route; for example, enterally, e.g., orally, e.g., in the form of tablets or capsules; parenterally, e.g., in the form of injectable solutions or suspensions; or topically, e.g., in the form of eye drops, lotions, gels, ointments or creams, or in a nasal or suppository form.

Pharmaceutical compositions comprising a compound of the present disclosure in free form or in a pharmaceutically acceptable salt form in association with at least one pharmaceutically acceptable carrier or diluent may be manufactured in a conventional manner by mixing, granulating, coating, dissolving or lyophilizing processes. For example, pharmaceutical compositions comprising a compound of the disclosure in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

In one embodiment, the pharmaceutical compositions are solutions of the active ingredient, including suspensions or dispersions, such as isotonic aqueous solutions. In the case of lyophilized compositions comprising the active ingredient alone or together with a carrier such as mannitol, dispersions or suspensions can be made up before use. The pharmaceutical compositions may be sterilized and/or contain adjuvants, such as preserving, stabilizing, wetting or emulsifying agents, solution promoters, salts for regulating the osmotic pressure and/or buffers. Suitable preservatives include but are not limited to antioxidants such as ascorbic acid, or microbicides, such as sorbic acid or benzoic acid. The solutions or suspensions may further comprise viscosity-increasing agents, including but not limited to, sodium carboxymethylcellulose, carboxymethylcellulose, dextran, polyvinylpyrrolidone, gelatins, or solubilizers, e.g. Tween 80 (polyoxyethylene(20)sorbitan mono-oleate).

Suspensions in oil may comprise as the oil component the vegetable, synthetic, or semi-synthetic oils customary for injection purposes. Examples include liquid fatty acid esters that contain as the acid component a long-chained fatty acid having from 8 to 22 carbon atoms, or in some embodiments, from 12 to 22 carbon atoms. Suitable liquid fatty acid esters include but are not limited to lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid and linoleic acid, and if desired, may contain antioxidants, for example vitamin E, 3-carotene or 3,5-di-tert-butyl-hydroxytoluene. The alcohol component of these fatty acid esters may have six carbon atoms and may be monovalent or polyvalent, for example a mono-, di- or trivalent, alcohol. Suitable alcohol components include but are not limited to methanol, ethanol, propanol, butanol or pentanol or isomers thereof; glycol and glycerol.

Other suitable fatty acid esters include but are not limited ethyl-oleate, isopropyl myristate, isopropyl palmitate, LABRAFIL® M 2375, (polyoxyethylene glycerol), LABRAFIL® M 1944 CS (unsaturated polyglycolized glycerides prepared by alcoholysis of apricot kernel oil and comprising glycerides and polyethylene glycol ester), LABRASOL™ (saturated polyglycolized glycerides prepared by alcoholysis of TCM and comprising glycerides and polyethylene glycol ester; all available from GaKefosse, France), and/or MIGLYOL® 812 (triglyceride of saturated fatty acids of chain length C8 to C12 from Hüls AG, Germany), and vegetable oils such as cottonseed oil, almond oil, olive oil, castor oil, sesame oil, soybean oil, or groundnut oil.

Pharmaceutical compositions for oral administration may be obtained, for example, by combining the active ingredient with one or more solid carriers, and if desired, granulating a resulting mixture, and processing the mixture or granules by the inclusion of additional excipients, to form tablets or tablet cores.

Suitable carriers include but are not limited to fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, carboxymethyl starch, crosslinked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

Tablet cores may be provided with suitable, optionally enteric, coatings through the use of, inter alia, concentrated sugar solutions which may comprise gum arable, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration may also include hard capsules comprising gelatin or soft-sealed capsules comprising gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient may be dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories comprising a combination of the active ingredient and a suppository base. Suitable suppository bases are, for example, natural or synthetic triglycerides, paraffin hydrocarbons, polyethylene glycols or higher alkanols.

Pharmaceutical compositions suitable for parenteral administration may comprise aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilizate and can be made into a solution before parenteral administration by the addition of suitable solvents. Solutions such as are used, for example, for parenteral administration can also be employed as infusion solutions. The manufacture of injectable preparations is usually carried out under sterile conditions, as is the filling, for example, into ampoules or vials, and the sealing of the containers.

The disclosure also provides for a pharmaceutical combinations, e.g. a kit, comprising a) a first agent which is a compound of the disclosure as disclosed herein, in free form or in pharmaceutically acceptable salt form, and b) at least one co-agent. The kit can comprise instructions for its administration.

Combination Therapies

The compounds or pharmaceutical acceptable salts of the disclosure may be administered as the sole therapy, or together with other therapeutic agent or agents.

For example, the therapeutic effectiveness of one of the compounds described herein may be enhanced by administration of an adjuvant (i.e. by itself the adjuvant may only have minimal therapeutic benefit, but in combination with another therapeutic agent, the overall therapeutic benefit to the individual is enhanced). Or, by way of example only, the benefit experienced by an individual may be increased by administering one of the compounds described herein with another therapeutic agent that also has therapeutic benefit. By way of example only, in a treatment for gout involving administration of one of the compounds described herein, increased therapeutic benefit may result by also providing the individual with another therapeutic agent for gout. Or, by way of example only, if one of the side effects experienced by an individual upon receiving one of the compounds described herein is nausea, then it may be appropriate to administer an anti-nausea agent in combination with the compound. Or, the additional therapy or therapies include, but are not limited to physiotherapy, psychotherapy, radiation therapy, application of compresses to a diseased area, rest, altered diet, and the like. Regardless of the disease, disorder or condition being treated, the overall benefit experienced by the individual may be additive of the two therapies or the individual may experience a synergistic benefit.

In the instances where the compounds described herein are administered in combination with other therapeutic agents, the compounds described herein may be administered in the same pharmaceutical composition as other therapeutic agents, or because of different physical and chemical characteristics, be administered by a different route. For example, the compounds described herein may be administered orally to generate and maintain good blood levels thereof, while the other therapeutic agent may be administered intravenously. Thus the compounds described herein may be administered concurrently, sequentially or dosed separately to other therapeutic agents.

EXAMPLES

Various methods may be developed for synthesizing a compound of formula (I) or a pharmaceutically acceptable salt thereof. Representative methods for synthesizing a compound of formula (I) or a pharmaceutically acceptable salt thereof are provided in the Examples. It is noted, however, that a compound of formula (I) or a pharmaceutically acceptable salt thereof may also be synthesized by other synthetic routes that others may devise.

It will be readily recognized that certain compounds of formula (I) have atoms with linkages to other atoms that confer a particular stereochemistry to the compound (e.g., chiral centers). It is recognized that synthesis of a compound of formula (I) or a pharmaceutically acceptable salt thereof may result in the creation of mixtures of different stereoisomers (enantiomers, diastereomers). Unless a particular stereochemistry is specified, recitation of a compound is intended to encompass all of the different possible stereoisomers.

A compound of formula (I) can also be prepared as a pharmaceutically acceptable acid addition salt by, for example, reacting the free base form of the at least one compound with a pharmaceutically acceptable inorganic or organic acid. Alternatively, a pharmaceutically acceptable base addition salt of the at least one compound of formula (I) can be prepared by, for example, reacting the free acid form of the at least one compound with a pharmaceutically acceptable inorganic or organic base. Inorganic and organic acids and bases suitable for the preparation of the pharmaceutically acceptable salts of compounds of formula (I) are set forth in the definitions section of this Application. Alternatively, the salt forms of the compounds of formula (I) can be prepared using salts of the starting materials or intermediates.

The free acid or free base forms of the compounds of formula (I) can be prepared from the corresponding base addition salt or acid addition salt form. For example, a compound of formula (I) in an acid addition salt form can be converted to the corresponding free base thereof by treating with a suitable base (e.g., ammonium hydroxide solution, sodium hydroxide, and the like). A compound of formula (I) in a base addition salt form can be converted to the corresponding free acid thereof by, for example, treating with a suitable acid (e.g., hydrochloric acid, etc).

The N-oxides of the a compound of formula (I) or a pharmaceutically acceptable salt thereof can be prepared by methods known to those of ordinary skill in the art. For example, N-oxides can be prepared by treating an unoxidized form of the compound of formula (I) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0 to 80° C. Alternatively, the N-oxides of the compounds of formula (I) can be prepared from the N-oxide of an appropriate starting material.

Compounds of formula (I) in an unoxidized form can be prepared from N-oxides of compounds of formula (I) by, for example, treating with a reducing agent (e.g., sulfur, sulfur dioxide, triphenyl phosphine, lithium borohydride, sodium borohydride, phosphorus trichloride, tribromide, and the like) in an suitable inert organic solvent (e.g., acetonitrile, ethanol, aqueous dioxane, and the like) at 0 to 80° C.

Protected derivatives of the compounds of formula (I) can be made by methods known to those of ordinary skill in the art. A detailed description of the techniques applicable to the creation of protecting groups and their removal can be found in T. W. Greene, Protecting Groups in Organic Synthesis, 3rd edition, John Wiley & Sons, Inc. 1999.

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. For example, the following abbreviations may be used in the examples and throughout the specification: g (grams); mg (milligrams); L (liters); mL (milliliters); µL (microliters); psi (pounds per square inch); M (molar); mM (millimolar); i.v. (intravenous); Hz (Hertz); MHz (megahertz); mol (moles); mmol (millimoles); RT (room temperature); min (minutes); h (hours); mp (melting point); TLC (thin layer chromatography); Rt (retention time); RP (reverse phase); MeOH (methanol); i-PrOH (isopropanol); TEA (triethylamine); TFA (trifluoroacetic acid); TFAA (trifluoroacetic anhydride); THF (tetrahydrofuran); DMSO (dimethyl sulfoxide); EtOAc (ethyl acetate); DME (1,2-dimethoxyethane); DCM (dichloromethane); DCE (dichloroethane); DMF (N,N-dimethylformamide); DMPU (N,N'-dimethylpropyleneurea); CDI (1,1-carbonyldiimidazole); IBCF (isobutyl chloroformate); HOAc (acetic acid); HOSu (N-hydroxysuccinimide); HOBT (1-hydroxybenzotriazole); Et$_2$O (diethyl ether); EDCI (1-(3-dimethylaminopropyl)-3-ethylcarbodiimide hydrochloride); BOC (tert-butyloxycarbonyl); FMOC (9-fluorenylmethoxycarbonyl); DCC (dicyclohexylcarbodiimide); CBZ (benzyloxycarbonyl); Ac (acetyl); atm (atmosphere); TMSE (2-(trimethylsilyl)ethyl); TMS (trimethylsilyl); TIPS (triisopropylsilyl); TBS (t-butyldimethylsilyl); DMAP (4-dimethylaminopyridine); Me (methyl); OMe (methoxy); Et (ethyl); tBu (tert-butyl); HPLC (high pressure liquid chomatography); BOP (bis(2-oxo-3-oxazolidinyl)phosphinic chloride); TBAF (tetra-n-butylammonium fluoride); m-CPBA (meta-chloroperbenzoic acid).

References to ether or Et$_2$O are to diethyl ether; brine refers to a saturated aqueous solution of NaCl. Unless otherwise indicated, all temperatures are expressed in ° C. (degrees Centigrade). All reactions were conducted under an inert atmosphere at RT unless otherwise noted.

$^1$H NMR spectra were recorded on a Varian Mercury Plus 400. Chemical shifts are expressed in parts per million (ppm). Coupling constants are in units of hertz (Hz). Splitting patterns describe apparent multiplicities and are designated as s (singlet), d (doublet), t (triplet), q (quartet), m (multiplet), and br (broad).

Low-resolution mass spectra (MS) and compound purity data were acquired on a Shimadzu LC/MS single quadrapole system equipped with electrospray ionization (ESI) source, UV detector (220 and 254 nm), and evaporative light scattering detector (ELSD). Thin-layer chromatography was performed on 0.25 mm Superchemgroup silica gel plates (60F-254), visualized with UV light, 5% ethanolic phosphomolybdic acid, ninhydrin, or p-anisaldehyde solution. Flash column chromatography was performed on silica gel (200-300 mesh, Branch of Qingdao Haiyang Chemical Co., Ltd).

Synthetic Schemes

A compound of formula (I) or a pharmaceutically acceptable salt thereof may be synthesized according to a variety of reaction schemes. Some illustrative schemes are provided below and in the examples. Other reaction schemes could be readily devised by those skilled in the art in view of the present disclosure.

In the reactions described herein after it may be necessary to protect reactive functional groups, for example hydroxyl, amino, imino, thio or carboxyl groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Synthetic methods for preparing the compounds of the present invention are illustrated in the following Schemes and Examples. Starting materials are commercially available or may be made according to procedures known in the art or as illustrated herein.

The intermediates shown in the following schemes are either known in the literature or may be prepared by a variety of methods familiar to those skilled in the art.

As an illustration, one synthesis of compounds of formula I of the present disclosure is outlined in Scheme 1. As shown in the Scheme, the compounds of formula I can be disassembled into the intermediates II and III, the preparation of which are either known in the literature or may be prepared by a variety of methods familiar to those skilled in the art. In the route, the intermediates II can be obtained via a three-step sequence including protection of free carboxyl group of IV, coupling with V and cleavage of the protecting groups. Finally, coupling of carboxylic acid II with aminoarenes such as those of formula III via a condensation reaction leads to compounds of formula I.

Scheme 1

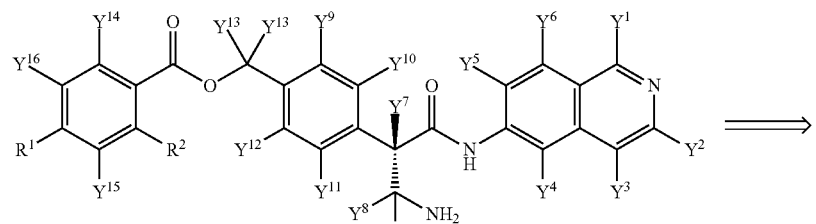

I

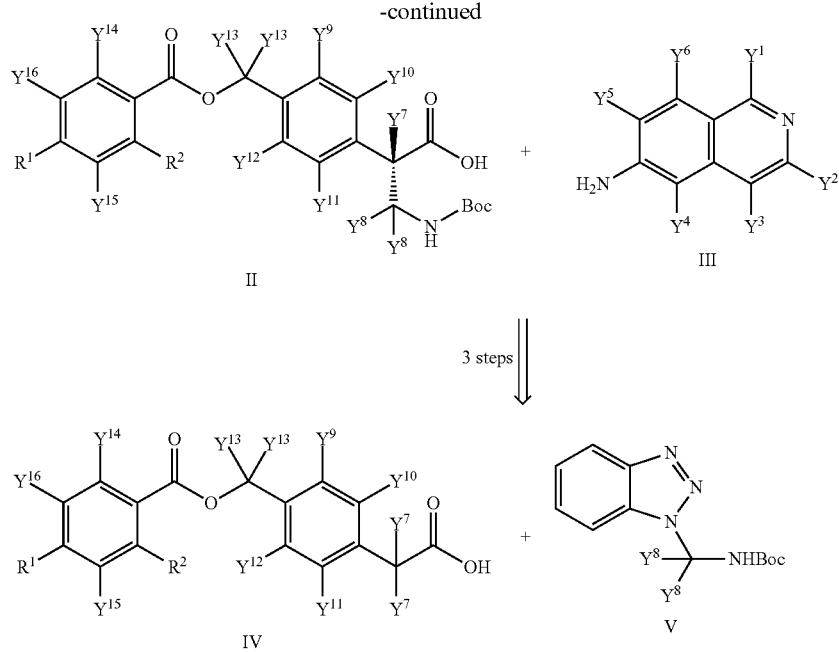

As an illustration of the preparation of intermediates of formula IV, one synthetic route of Intermediate IVa is shown in Scheme 2. Starting from the commercially available IVa-A. IVa-C can be prepared by carbonyl insertion reaction and TBS protection of free hydroxyl group of IVa-B. Reduction of ester IVa-C with $LiAlD_4$ leads to IVa-D, which can be further converted to IVa-E through a condensation with benzoic acid VI. Finally, Intermediate of formula IVa can be obtained from IVa-E through a sequence of cleavage of the protecting groups on the oxygen and oxidation of the resulting alcohol.

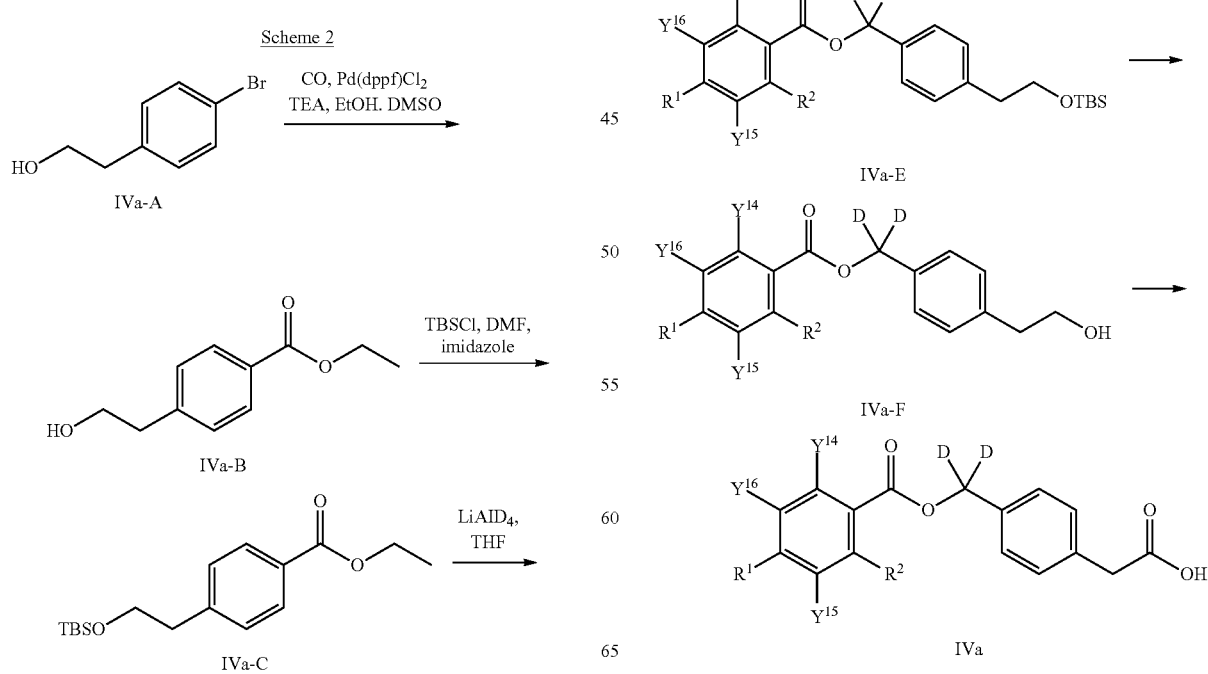

As a further illustration of the preparation of intermediates of formula IV, one synthetic route of intermediate IVb is provided in Scheme 3 The commercially available dimethyl terephthalate IVb-A is selected as starting material. Reduction of IVb-A with LiAlD₄ leads to IVb-B, which can be further converted to IVb-D through selective TBDPS protection of the hydroxyl group and iodination The nucleophilic displacement of the iodide of IVb-D with TMSCN yields intermediate IVb-E. Conversion of the cyano group in IVb-E into methyl ester group results in intermediate of formula IVb-G. Finally, Compounds of formula IVb can be prepared by condensation with benzoic acid VI followed by hydrolysis of IVb-H.

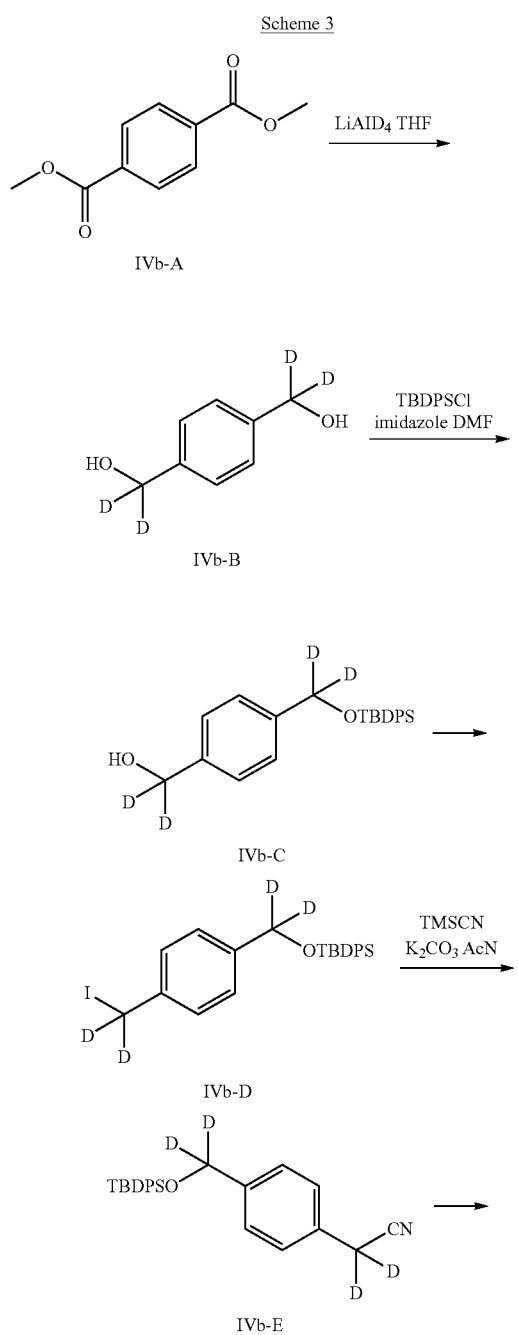

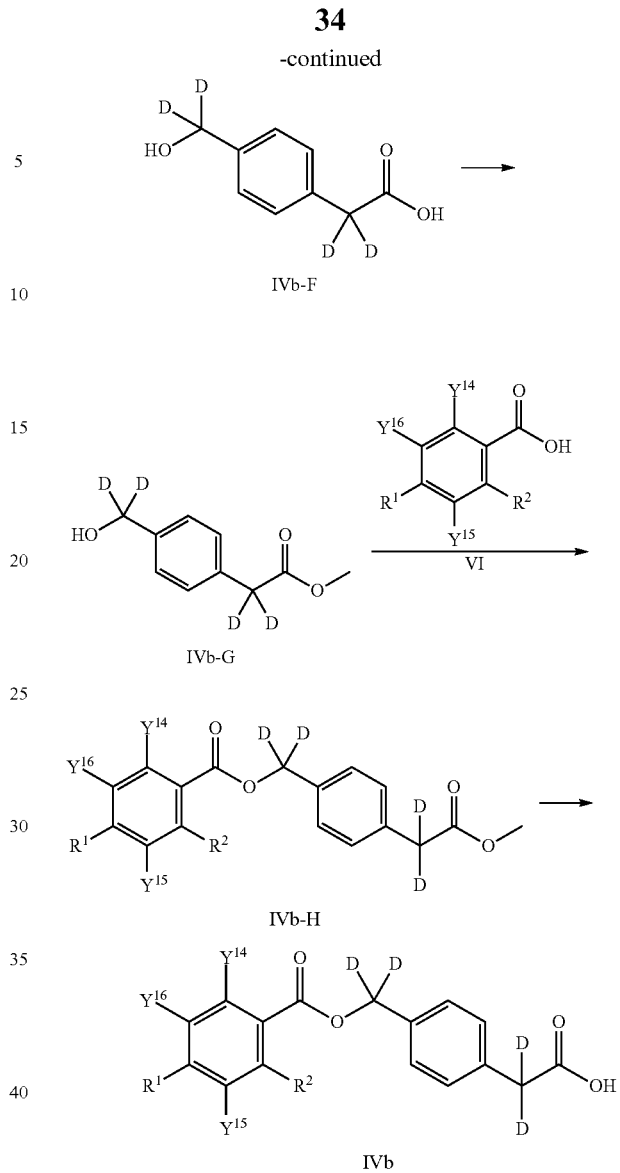

Another illustration of the preparation of intermediates of formula IV is shown is Scheme 4 which demonstrates preparation of compound of formula IVc. Starting from commercially available 2,4-dimethylbenzoic acid IVc-A. The intermediate 2,4-bis(methyl-d₃)benzoic acid IVc-B can be prepared by treating IVc-A with t-BuOK and DMSO-d₆. Coupling of 2,4-bis(methyl-d₃)benzoic acid IVc-B with the intermediates of formula IVc-C via a condensation reaction leads to compounds of formula IVc-D. Finally, hydrolysis of IVc-D results in compounds of formula IVc.

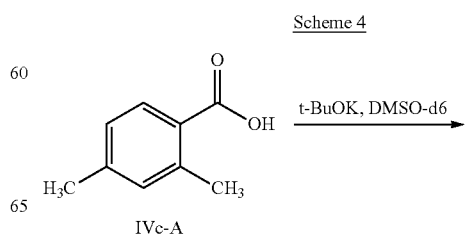

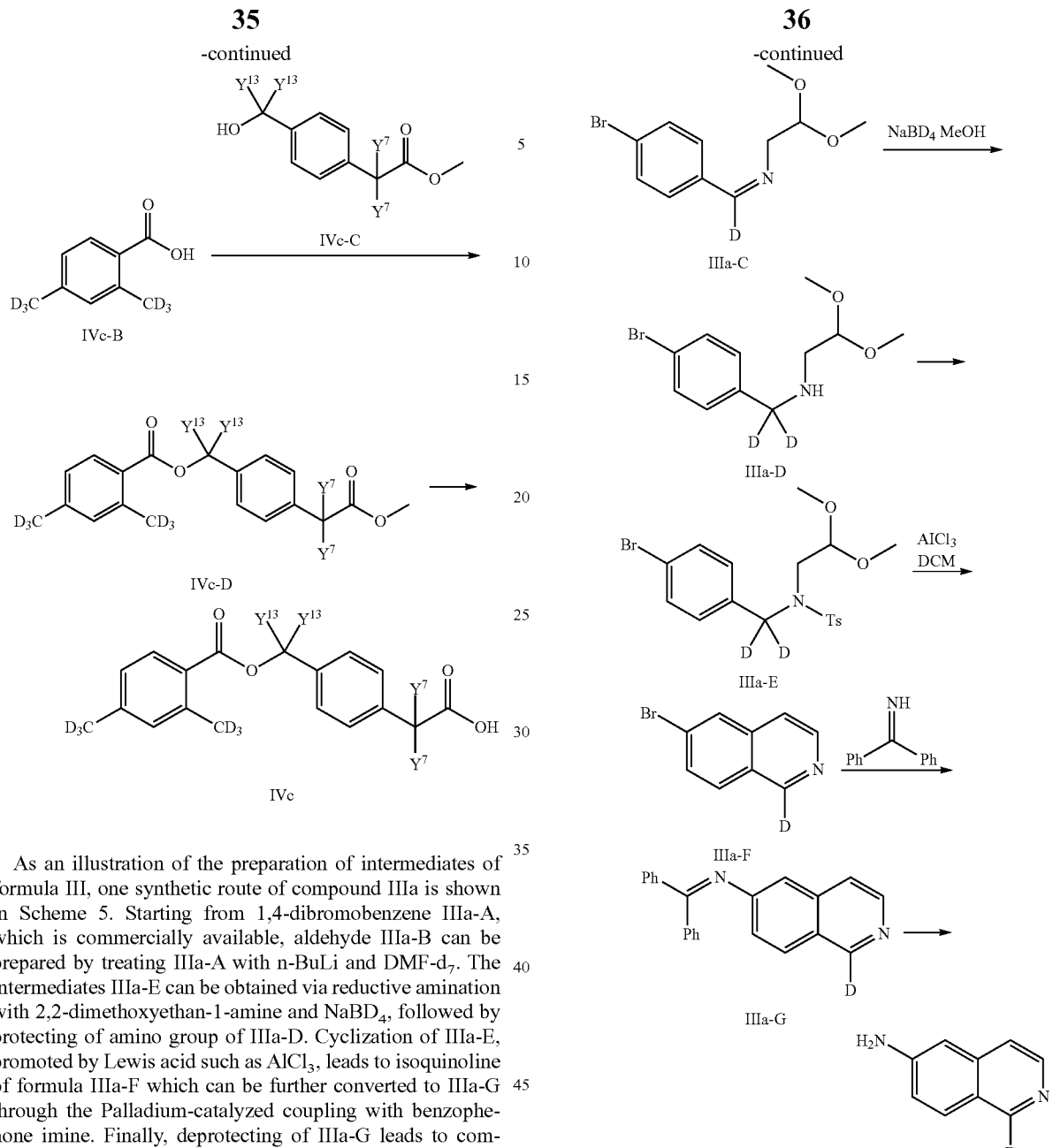

As an illustration of the preparation of intermediates of formula III, one synthetic route of compound IIIa is shown in Scheme 5. Starting from 1,4-dibromobenzene IIIa-A, which is commercially available, aldehyde IIIa-B can be prepared by treating IIIa-A with n-BuLi and DMF-d$_7$. The intermediates IIIa-E can be obtained via reductive amination with 2,2-dimethoxyethan-1-amine and NaBD$_4$, followed by protecting of amino group of IIIa-D. Cyclization of IIIa-E, promoted by Lewis acid such as AlCl$_3$, leads to isoquinoline of formula IIIa-F which can be further converted to IIIa-G through the Palladium-catalyzed coupling with benzophenone imine. Finally, deprotecting of IIIa-G leads to compounds of formula IIIa.

Scheme 5

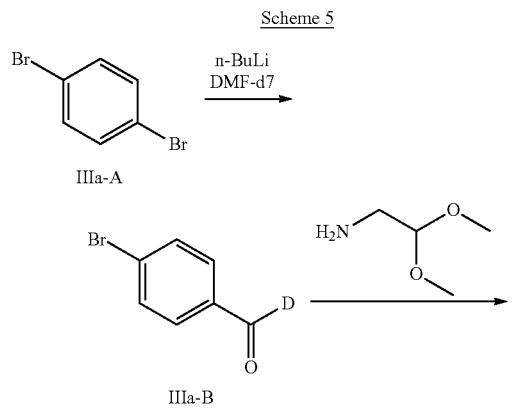

As a further illustration of the preparation of intermediates of formula III, one synthetic route of compound IIIb is shown in Scheme 6. Starting from commercially available 2-oxoacetic acid IIIb-A. The intermediate IIIb-B can be prepared by treating IIIb-A with trimethoxymethane and p-TsOH. Ammonolysis of IIIb-B gives compounds of formula IIIb-C which can be further transformed into compounds of formula IIIb-D via reduction of amide with LiAlD$_4$. The intermediate IIIb-G can be obtained from the intermediate IIIb-D via reductive amination with 4-bromobenzaldehyde and NaBH$_4$, followed by protecting of amino group of IIIb-F. Cyclization of IIIb-G, promoted by Lewis acid such as AlCl$_3$, leads to isoquinoline of formula IIIb-H which can be further converted to IIIb-I through the Palladium-catalyzed coupling with benzophenone imine. Finally, deprotecting of IIIb-I leads to compounds of formula IIIb.

37

Scheme 6

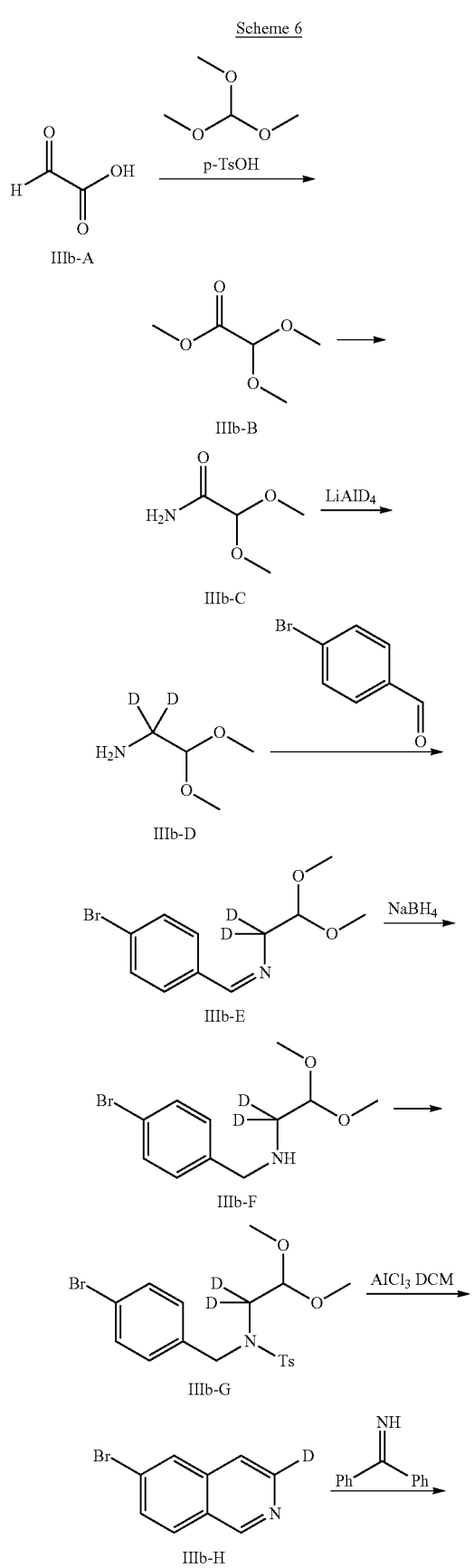

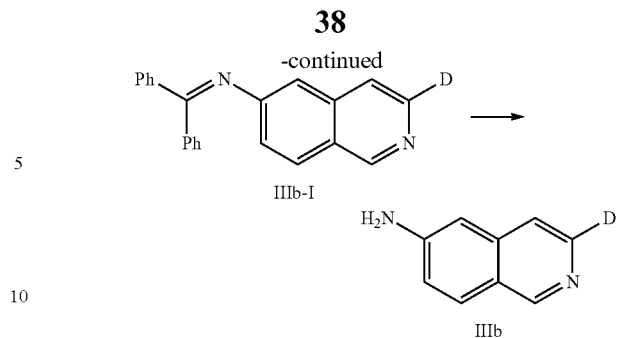

As an illustration of the preparation of intermediates of formula V, one synthetic route of compound Va is shown in Scheme 7. Starting from commercially available 1H-benzo[d][1,2,3]triazole Va-A. The intermediates Va-B can be prepared by treating Va-A with formaldehyde-$d_2$. Then compounds of formula Va can be obtained via a conversion of the hydroxyl group in Va-B into the Boc-protected amino group with tert-butyl carbamate and 4-methylbenzenesulfonic acid.

Scheme 7

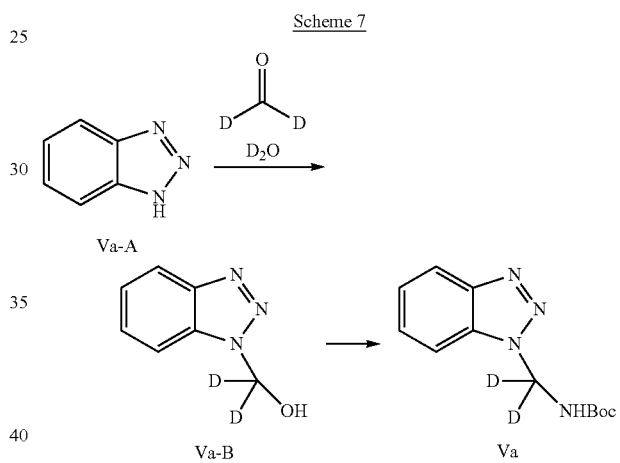

In some cases, the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Intermediate A

Isoquinolin-1-d-6-amine (A)

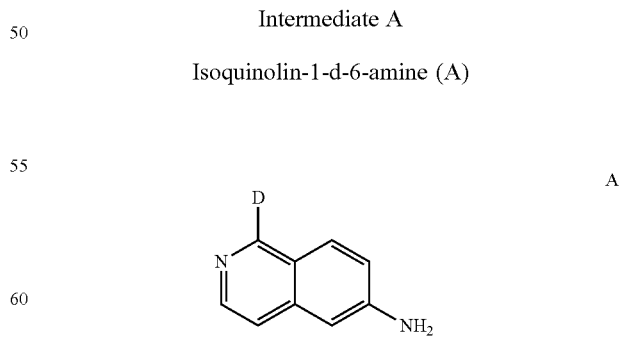

(4-Bromophenyl)-deuterio-methanone (A1)

To a solution of 1,4-dibromobenzene (2.50 g, 10.6 mmol) in THF (5 mL) at −78° C. was added n-BuLi (1.6 M, 7 mL, 11.7 mmol) dropwise, and the resulting mixture was stirred at −78° C. for 0.5 h. Then DMF-$d_7$ (1.08 mL, 12.7 mmol) was added dropwise to the mixture at −78° C. and the resulting mixture was stirred at −78° C.~−30° C. for 1.5 h. The reaction was quenched with saturated aqueous NH$_4$Cl (2 mL) at −30° C. The mixture was diluted with water and extracted with EtOAc (3×50 mL). The extracts were washed with brine, dried over Na$_2$SO$_4$ and concentrated to give the crude product of title compound (4-bromophenyl)-deuterio-methanone (A1), which was used without further purification for next step.

N-((4-bromophenyl)methyl-$d_2$)-2,2-dimethoxyethan-1-amine (A2)

A mixture of (4-bromophenyl)-deuterio-methanone (A1) (2.00 g, 10.8 mmol), p-TsOH.H$_2$O (0.210 g, 1.08 mmol) and 2,2-dimethoxyethan-1-amine (1.05 g, 10.0 mmol) in toluene (30 mL) was stirred at 138° C. for 3.5 h. The mixture was poured into saturated NaHCO$_3$ aqueous solution (8 mL), washed sequentially with aqueous NaHCO$_3$ solution (2×100 mL) and water (1×100 mL), and the aqueous phase was extracted with toluene (2×100 mL). The combined organic phase was dried over Na$_2$SO$_4$ and concentrated. The residue was dissolved in EtOH (20 mL), then NaBD$_4$ (220 mg, 5.50 mmol) was added to the mixture at RT and the resulting mixture was stirred at RT for 2 h. Then HOAc (0.2 mL) was added to the mixture. The reaction mixture was diluted with water and extracted with EtOAc. The extracts were washed with brine, dried over Na$_2$SO$_4$ and concentrated to give the crude product of title compound N-((4-bromophenyl)methyl-$d_2$)-2,2-dimethoxyethan-1-amine (A2). MS-ESI (m/z): 276 [M+1]$^+$.

N-((4-bromophenyl)methyl-$d_2$)-N-(2,2-dimethoxyethyl)-4-methylbenzenesulfonamide (A3)

To a solution of N-((4-bromophenyl)methyl-$d_2$)-2,2-dimethoxyethan-1-amine (A2) (2.5 g, 9.1 mmol) in DCM (16 mL) and pyridine (2 mL) was added TsCl (3.10 g, 16.3 mmol). The mixture was stirred at RT for 2 h. The mixture was washed with 1 N HCl (3×50 mL), dried and concentrated. The residue was purified by column chromatography on silica gel, eluting with PE/EtOAc (20:1~5:1) to give the title compound N-((4-bromophenyl)methyl-$d_2$)-N-(2,2-dimethoxyethyl)-4-methylbenzenesulfonamide (A3). MS-ESI (m/z): 430 [M+1]$^+$.

6-Bromoisoquinoline-1-d (A4)

To a mixture of AlCl$_3$ (2.95 g, 22.0 mmol) in DCM (10 mL) was added a solution of N-((4-bromophenyl)methyl-$d_2$)-N-(2,2-dimethoxyethyl)-4-methylbenzenesulfonamide (A3) (1.9 g, 4.4 mmol) in DCM (10 mL) dropwise. After being stirred at RT for 4 h. the mixture was poured into ice (50 g), and extracted with DCM (3×100 mL). The organic phase was washed sequentially with 1 N NaOH (2×100 mL), aqueous NaHCO$_3$ solution (1×100 mL) and brine (100 mL), dried and concentrated. The residue was purified by column chromatography on silica gel, eluting with PE/EtOAc (5:1) to give the title compound 6-bromoisoquinoline-1-d (A4). MS-ESI (m/z): 209 [M+1]$^+$.

Isoquinolin-1-d-6-amine (A)

To a mixture of 6-bromoisoquinoline-1-d A4) (455 mg, 2.19 mmol), diphenylmethanimine (441 μl, 2.62 mmol) and t-BuONa (631 mg, 6.57 mmol) in toluene (10 mL) was added BINAP (954 mg, 1.53 mmol) and Pd$_2$(dba)$_3$ (401 mg, 0.438 mmol) at RT. The mixture was stirred at 100° C. for 3 h. The mixture was concentrated. The residue was dissolved in MeOH (20 mL), then NH$_2$OH.HCl (241 mg, 3.50 mmol) and NaOAc (312 mg, 3.80 mmol) was added to the mixture at RT and the resulting mixture was stirred at RT for 1.5 h. The mixture was concentrated and the residue was purified by column chromatography on silica gel, eluting with PE/EtOAc (1:1) to give the title compound isoquinolin-1-d-6-amine (A). MS-ESI (m/z): 146 [M+1]$^+$.

Intermediate B isoquinolin-3-d-6-amine (B-a) and isoquinolin-3,4-d2-6-amine (B-b)

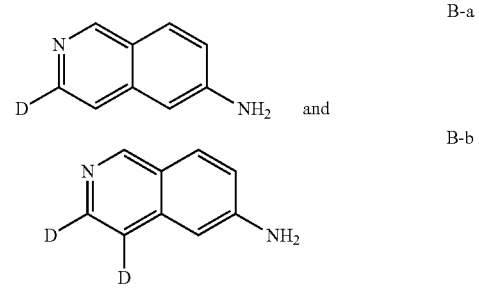

2,2-dimethoxyethan-1,1-$d_2$-1-amine (B1)

To a solution of 2,2-dimethoxyacetamide (0.10 g, 0.84 mmol) in THF (3 mL) was added LiAlD$_4$ (42 mg, 1.0 mmol) at RT, and the mixture was stirred at 65° C. for 1.5 h. Then NaSO$_4$.10H$_2$O was added to the mixture under ice water bath. After being stirred for 20 min, the mixture was filtered. The filtered cake was washed with THF and the solution was evaporated to give the crude product of 2,2-dimethoxyethan-1,1-$d_2$-1-amine (B), which was used for next step without further purification. MS-ESI (m/z): 108 [M+1]$^+$.

N-(4-bromobenzyl)-2,2-dimethoxyethan-1,1-$d_2$-1-amine (B2)

A mixture of 2,2-dimethoxyethan-1,1-$d_2$-1-amine (B1) (100 mg, 0.920 mmol), p-TsOH.H$_2$O (17.5 mg, 0.0920 mmol) and 4-bromobenzaldehyde (170 mg, 0.920 mmol) in toluene (50 mL) was stirred at 135° C. for 4.5 h. After being concentrated, the residue was dissolved in EtOH (30 mL), then NaBH$_4$ (300 mg, 7.90 mmol) was added to the mixture at RT. The resulting mixture was stirred at RT for 1 h. Then HOAc (0.2 mL) was added to the mixture. Solvent was concentrated, the residue was diluted with water and extracted with EtOAc. The extracts were washed with brine, dried over Na$_2$SO$_4$ and concentrated to give the crude product of title compound N-(4-bromobenzyl)-2,2-dimethoxyethan-1,1-$d_2$-1-amine (B2). MS-ESI (m/z): 276 [M+1]$^+$.

isoquinolin-3-d-6-amine (B-a) and isoquinolin-3,4-$d_2$-6-amine (B-b)

The title compound isoquinolin-3-d-6-amine (B-a) (30%) and isoquinolin-3,4-$d_2$-6-amine (B-b) (70%) was prepared according to the synthetic method of A by replacing N-((4-bromophenyl)methyl-d$_2$)-2,2-dimethoxyethan-1-amine (A2) with N-(4-bromobenzyl)-2,2-dimethoxyethan-1,1-d$_2$-1-amine (B2). MS-ESI (m/z) B-a: 146 [M+1]$^+$ and B-b: 147 [M+1]$^+$ Intermediate C 2,4-Bis(methyl-d$_3$)benzoic acid (C)

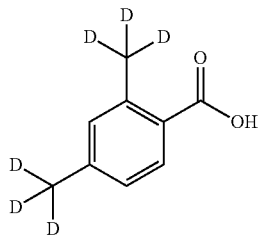

2,4-Bis(methyl-d$_3$)benzoic acid (C)

To a solution of 2,4-dimethylbenzoic acid (1.0 g, 6.1 mmol) in DMSO-d$_6$ (10 mL) was added t-BuOK (3.40 g, 30.5 mmol). The mixture was stirred at 120° C. under N$_2$ for 3 h. After cooled to RT, the mixture was diluted with water. The pH was adjusted to 2~3 and extracted with EtOAc (3×). The extracts were washed with water, brine, dried over Na$_2$SO$_4$ and concentrated to give a solid. This solid was treated for 2 times according to the above process to give the title compound 2,4-bis(methyl-d$_3$)benzoic acid (C).

Intermediate D (4-(2-((tert-butyldimethylsilyl)oxy)ethyl)phenyl)methan-d$_2$-ol (D)

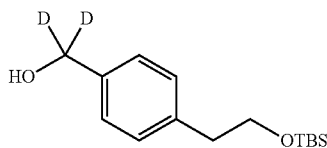

Ethyl 4-(2-hydroxyethyl)benzoate (D1)

A mixture of 2-(4-bromophenyl)ethan-1-ol (1.0 g, 5.0 mmol), TEA (0.83 ml, 6.0 mmol) and Pd(dppf)Cl$_2$ (365 mg, 0.500 mmol) in EtOH (35 mL) and DMSO (22 mL) was stirred at 80° C. under CO atmosphere for 3.5 h. The reaction mixture was cooled to RT, quenched with saturated aqueous NH$_4$Cl solution and extracted with EtOAc. The extracts were washed with brine (30 mL), dried over Na$_2$SO$_4$ and concentrated. The residue was purified by column chromatography on silica gel eluting with PE/EtOAc (5:1~4:1) to give the title compound ethyl 4-(2-hydroxyethyl)benzoate (D1). MS-ESI (m/z): 195 [M+1]$^+$.

Ethyl 4-(2-((tert-butyldimethylsilyl)oxy)ethyl)benzoate (D2)

To a solution of ethyl 4-(2-hydroxyethyl)benzoate (D) (0.96 g, 4.9 mmol) in DMF (20 mL) was added imidazole (0.84 g, 12 mmol). The mixture was cooled to 0° C. and then TBSCl (0.894 g, 5.91 mmol) was added. The mixture was stirred at RT for 30 min, diluted with water and extracted with EtOAc. The extracts were washed with brine (30 mL), dried over Na$_2$SO$_4$ and concentrated. The residue was purified by column chromatography on silica gel eluting with PE/EtOAc (50:1) to give the title compound ethyl 4-(2-((tert-butyldimethylsilyl)oxy)ethyl) benzoate (D2). MS-ESI (m/z): 309 [M+1]$^+$.

(4-(2-((tert-butyldimethylsilyl)oxy)ethyl)phenyl)methan-d$_2$-ol (D)

The title compound (4-(2-((tert-butyldimethylsilyl)oxy)ethyl)phenyl)methan-d$_2$-ol (D) was prepared according to the synthetic method of 2,2-dimethoxyethan-1,1-d$_2$-1-amine (B1) by replacing 2,2-dimethoxyacetamide with ethyl 4-(2-((tert-butyldimethylsilyl)oxy)ethyl)-benzoate (D2). MS-ESI (m/z): 269 [M+1]$^+$.

Intermediate E

Methyl 2-(4-(hydroxymethyl-d$_2$)phenyl)acetate-d$_2$ (E)

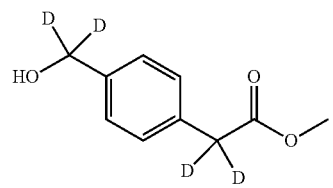

1,4-Phenylenebis(methan-d$_2$-ol) (E1)

To a solution of dimethyl terephthalate (5.9 g, 30 mmol) in THF (100 mL) at 0° C., was added LiAlD$_4$ (3.5 g, 59 mmol) with several portions. The mixture was stirred at 65° C. for 1 h. After being cooled to 0° C., the mixture was quenched with Na$_2$SO$_4$10H$_2$O carefully and filtered. The filtrate was concentrated to give the title compound 1,4-phenylenebis(methan-d$_2$-ol) (E1).

(4-(((Tert-butyldimethylsilyl)oxy)methyl-d$_2$)phenyl)methan-d$_2$-ol (E2)

To a solution of 1,4-phenylenebis(methan-d$_2$-ol) (E1) (4.3 g, 30 mmol) and 1H-imidazole (2.2 g, 33 mmol) in DMF (50 mL) was added tert-butylchlorodimethylsilane (8.3 g, 30 mmol) dropwise. After being stirred at RT for 18 h, the mixture was poured into H$_2$O, and extracted with EtOAc (3×). The extracts were washed with H$_2$O, brine, dried over Na$_2$SO$_4$ and concentrated to give the title compound (4-(((tert-butyldimethylsilyl)oxy)methyl-d$_2$)phenyl)methan-d$_2$-ol (E2).

Tert-butyl((4-(iodomethyl-d$_2$)phenyl)methoxy-d$_2$)dimethylsilane (E3)

A mixture of (4-(((tert-butyldimethylsilyl)oxy)methyl-d$_2$)phenyl)methan-d$_2$-ol (E2) (3.8 g, 10 mmol), 1H-imidazole (1.05 g, 15.0 mmol), iodine (3.3 g, 13 mmol) and triphenylphosphane (3.9 g, 15 mmol) in DCM (60 mL) was stirred at RT under N$_2$ atmosphere for 5 h. The mixture was diluted with DCM, washed with Na$_2$S$_2$O$_3$ aqueous solution and brine, dried over Na$_2$SO$_4$ and concentrated. The residue was purified by column chromatography on silica gel, eluting with PE/EtOAc (10:1) to give the title compound tert-butyl((4-(iodomethyl-d$_2$)phenyl)methoxy-d$_2$)dimethylsilane (E3).

2-(4-(((Tert-butyldimethylsilyl)oxy)methyl-d$_2$)phenyl)acetonitrile-d$_2$ (E4)

To a mixture of tert-butyl((4-(iodomethyl-d$_2$)phenyl)methoxy-d$_2$)dimethylsilane (E4) (3.6 g, 7.3 mmol) and K$_2$CO$_3$ (1.8 g, 13 mmol) in acetonitrile (40 mL) was added TMSCN (1.6 mL, 13 mmol). After being refluxed for 20 h, the mixture was cooled to RT and filtered. The filtrate was concentrated. The residue was purified by column chromatography on silica gel, eluting with PE/EtOAc (10:1) to give the title compound 2-(4-(((tert-butyldimethylsilyl)oxy)methyl-d$_2$)phenyl)acetonitrile-d$_2$ (E5).

2-(4-(Hydroxymethyl-d$_2$)phenyl)acetic-2,2-d$_2$ acid (E6)

To a solution of NaH (5.00 g, 120 mmol) in D$_2$O (20 ml) was added 2-(4-(((tert-butyldimethylsilyl)oxy)methyl-d$_2$)phenyl)acetonitrile-d$_2$ (E5) (2.5 g, 6.0 mmol) in EtOD (20 mL). The mixture was stirred at 80° C. for 15 h. After cooling to RT, the mixture was diluted with D$_2$O (30 ml), adjusted pH to 2~3 and extracted with EtOAc (3×). The extracts were washed with brine and dried over Na$_2$SO$_4$. The solvents were concentrated to give the title compound 2-(4-(hydroxymethyl-d$_2$)phenyl)acetic-2,2-d$_2$ acid (E6). MS-ESI (m/z): 169 [M−1]$^-$.

Methyl 2-(4-(hydroxymethyl-d$_2$)phenyl)acetate-d$_2$ (E)

To a solution of 2-(4-(hydroxymethyl-d$_2$)phenyl)acetic-2,2-d$_2$ acid (E6) (1.35 g, 7.94 mmol) in MeOH (13 mL) was added Con.H$_2$SO$_4$ (1.3 mL) dropwise. The mixture was stirred at RT for overnight. The mixture was poured into water, and extracted with EtOAc (3×). The extracts were washed with sat. NaHCO$_3$ (aqueous solution) and brine, dried over Na$_2$SO$_4$, and concentrated to give the title compound methyl 2-(4-(hydroxymethyl-d$_2$)phenyl)acetate-d$_2$ (E). MS-ESI (m/z): 185 [M+1]$^+$.

Intermediate F

Tert-butyl ((1H-benzo[d][1,2,3]triazol-1-yl)methyl-d2)carbamate (F)

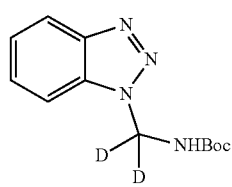

F (1H-benzo[d][1,2,3]triazol-1-yl)methan-d$_2$-ol (F1)

To a solution of 1H-benzo[d][1,2,3]triazole (625 mg, 5.25 mmol) in H$_2$O (40 mL) was added formaldehyde-d$_2$ (20% in D$_2$O) (840 mg, 5.25 mmol). The mixture was stirred at RT for 3 h. The solid was collected by filtration, and dried to give the title compound (1H-benzo[d][1,2,3]triazol-1-yl)methan-d$_2$-ol (F1). MS-ESI (m/z): 152 [M+1]$^+$.

Tert-butyl ((1H-benzo[d][1,2,3]triazol-1-yl)methyl-d$_2$)carbamate (F)

A mixture of (1H-benzo[d][1,2,3]triazol-1-yl)methan-d$_2$-ol (F1) (650 mg, 4.28 mmol), tert-butyl carbamate (500 mg, 4.28 mmol) and 4-methylbenzenesulfonic acid (26.7 mg, 0.155 mmol) in toluene (50 mL) was refluxed using Dean-Stark trap for 1 h. After being cooled to RT, the mixture was concentrated to ¼ volume. Then, the solid was collected by filtration, and dried to give the title compound tert-butyl ((1H-benzo[d][1,2,3]triazol-1-yl)methyl-d$_2$)carbamate (F). MS-ESI (m/z): 251 [M+1]$^+$.

Example 1

(S)-4-(3-amino-1-((isoquinolin-6-yl-1-d)amino)-1-oxopropan-2-yl)benzyl 2,4-dimethylbenzoate (1)

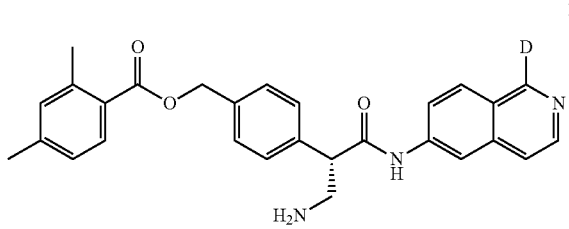

1

(S)-3-((tert-butoxycarbonyl)amino)-2-(4-(((2,4-dimethylbenzoyl)oxy)methyl)phenyl)-propanoic acid (1a)

(S)-3-((tert-butoxycarbonyl)amino)-2-(4-(((2,4-dimethylbenzoyl)oxy)methyl)-phenyl)propanoic acid (1a) was prepared according to the method described in WO2017/086941.

(S)-4-(3-((tert-butoxycarbonyl)amino)-1-((isoquinolin-6-yl-1-d)amino)-1-oxopropan-2-yl)benzyl 2,4-dimethylbenzoate (1b)

To a mixture of (S)-3-((tert-butoxycarbonyl)amino)-2-(4-(((2,4-dimethylbenzoyl)-oxy)methyl)phenyl)propanoic acid (1a) (56 mg, 0.13 mmol), isoquinolin-1-d-6-amine (A) (25 mg, 0.17 mmol) and 2,4-lutidine (18 mg, 0.17 mmol) in DMF (1 mL) was added 1,1,1-trichloro-2-methylpropan-2-yl carbonochloridate (41 mg, 0.17 mmol) and stirred at RT for 3 h. The mixture was poured into water (20 mL), extracted with EtOAc (3×50 mL), washed with brine (15 mL), dried over Na$_2$SO$_4$ and concentrated. The residue was purified by preparative TLC, eluting with DCM/MeOH (15:1) to give (S)-4-(3-((tert-butoxycarbonyl)amino)-1-((isoquinolin-6-yl-1-d) amino)-1-oxopropan-2-yl)benzyl 2,4-dimethylbenzoate (1b). MS-ESI (m/z): 555 [M+1]$^+$.

(S)-4-(3-amino-1-((isoquinolin-6-yl-1-d)amino)-1-oxopropan-2-yl)benzyl 2,4-dimethylbenzoate (1)

To a mixture of (S)-4-(3-((tert-butoxycarbonyl)amino)-1-((isoquinolin-6-yl-1-d)-amino)-1-oxopropan-2-yl)benzyl 2,4-dimethylbenzoate (1b) (25 mg, 0.050 mmol) in DCM (5 mL) was added TFA (1 mL) dropwise. The mixture was stirred at RT for 1 h. The mixture was poured into saturated $NaHCO_3$ and extracted with DCM (3×30 mL). The organic layer was washed with brine, dried over $Na_2SO_4$ and concentrated. The residue was purified by preparative TLC eluting with $DCM/NH_3$ in MeOH (20:1) to give (S)-4-(3-amino-1-((isoquinolin-6-yl-1-d)amino)-1-oxopropan-2-yl) benzyl 2,4-dimethylbenzoate (1). MS-ESI (m/z): 455 $[M+1]^+$.

Example 2

(S)-4-(3-amino-1-((isoquinolin-6-yl-3-d)amino)-1-oxopropan-2-yl)benzyl 2,4-dimethylbenzoate (2-A) and (S)-4-(3-amino-1-((isoquinolin-6-yl-3,4-$d_2$)amino)-1-oxopropan-2-yl)benzyl 2,4-dimethylbenzoate (2-B)

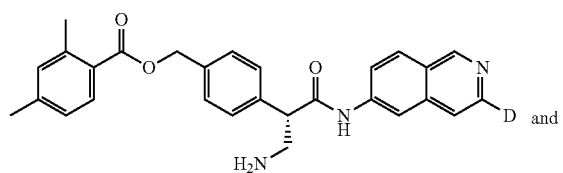

2-A

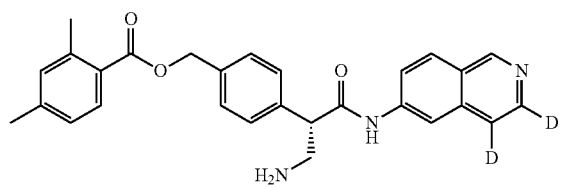

2-B

(S)-4-(3-amino-1-((isoquinolin-6-yl-3-d)amino)-1-oxopropan-2-yl)benzyl 2,4-dimethylbenzoate (2)

The title compound (S)-4-(3-amino-1-((isoquinolin-6-yl-3-d)amino)-1-oxopropan-2-yl)benzyl 2,4-dimethylbenzoate (2-A) (30%) and (S)-4-(3-amino-1-((isoquinolin-6-yl-3,4-$d_2$)amino)-1-oxopropan-2-yl)benzyl 2,4-dimethylbenzoate (2-B) (70%) was prepared according to the synthetic method of (S)-4-(3-amino-1-((isoquinolin-6-yl-1-d)amino)-1-oxopropan-2-yl) 2,4-dimethyl-benzoate (1) by replacing isoquinolin-1-d-6-amine (A) with isoquinolin-3-d-6-amine (B-a) and isoquinolin-3,4-$d_2$-6-amine (B-b). MS-ESI (m/z): 2-A: 455 $[M+1]^+$ and 2-B: 456 $[M+1]^+$

Example 3

(S)-(4-(3-amino-1-(isoquinolin-6-ylamino)-1-oxopropan-2-yl)phenyl)methyl-$d_2$ 2,4-dimethylbenzoate (3)

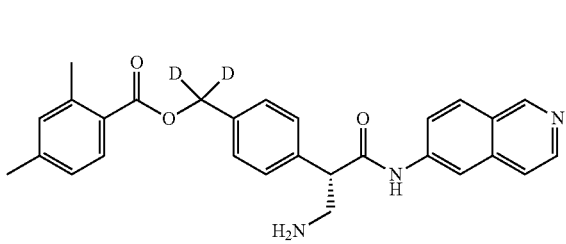

3

(4-(2-((tert-Butyldimethylsilyl)oxy)ethyl)phenyl)methyl-$d_2$ 2,4-dimethylbenzoate (3a)

To a solution of 2,4-dimethylbenzoic acid (31.0 mg, 0.204 mmol) in DCM (1 mL) was added EDCI (65.0 mg, 0.335 mmol). The mixture was stirred at RT for 1 h, and then, a solution of (4-(2-((tert-butyldimethylsilyl)oxy)ethyl)phenyl)methan-$d_2$-ol (D) (50.0 mg, 0.186 mmol) in DCM and DMAP (5.0 mg, 0.0372 mmol) were added. The mixture was stirred at RT for overnight. The mixture was diluted with water and extracted with DCM (3×25 mL). The extracts were washed with brine (15 mL), dried over $Na_2SO_4$ and concentrated. The residue was purified by column chromatography on silica gel, eluting with PE/EtOAc (50:1) to give the title compound (4-(2-((tert-butyldimethylsilyl)oxy) ethyl)-phenyl)methyl-$d_2$ 2,4-dimethylbenzoate (3a). MS-ESI (m/z): 401 $[M+1]^+$.

(4-(2-Hydroxyethyl)phenyl)methyl-$d_2$ 2,4-dimethylbenzoate (3b)

To a solution of (4-(2-((tert-butyldimethylsilyl)oxy)ethyl) phenyl)methyl-$d_2$ 2,4-dimethylbenzoate (3a) (4.100 g, 10.25 mmol) in MeOH (20 mL) was added 1 N HCl (2 mL). The mixture was stirred at RT for 1 h. The mixture was diluted with water and extracted with DCM (3×25 mL). The extracts were washed with brine, dried over $Na_2SO_4$ and concentrated to give the title compound (4-(2-hydroxyethyl)phenyl)methyl-$d_2$ 2,4-dimethylbenzoate (3b). MS-ESI (m/z): 287 $[M+1]^+$.

(4-(2-Oxoethyl)phenyl)methyl-$d_2$ 2,4-dimethylbenzoate (3c)

To a solution of (4-(2-hydroxyethyl)phenyl)methyl-$d_2$ 2,4-dimethylbenzoate (3b) (2.90 g, 10.3 mmol) in DCM (100 mL) was added DMP (5.20 g, 12.3 mmol). The mixture was stirred at RT for 30 min. The reaction was quenched with saturated aqueous $NaHCO_3$ solution (100 mL) and extracted with DCM. The organic phase was washed with brine (20 mL), dried over $Na_2SO_4$ and concentrated. The residue was purified by column chromatography on silica gel, eluting with PE/EtOAc (10:1) to give the title compound (4-(2-oxoethyl)phenyl)methyl-$d_2$ 2,4-dimethylbenzoate (3c). MS-ESI (m/z): 285 $[M+1]^+$.

2-(4-(((2,4-Dimethylbenzoyl)oxy)methyl-d$_2$)phenyl)
acetic acid (3d)

To a solution of (4-(2-oxoethyl)phenyl)methyl-d$_2$ 2,4-dimethylbenzoate (3c) (50 mg, 0.18 mmol) in DMF (1 mL) was added Oxone (36 mg, 0.21 mmol). The mixture was stirred at RT for 4 h. The mixture was poured into water (20 mL). The precipitated solid was collected by filtration, washed with water (30 mL) and dried to give the crude product of 2-(4-(((2,4-dimethylbenzoyl)oxy)-methyl-d$_2$)phenyl)acetic acid (3d), which was used for next step without further purification. MS-ESI (m/z): 301 [M+1]$^+$.

(4-(2-Chloro-2-oxoethyl)phenyl)methyl-d$_2$ 2,4-dimethylbenzoate (3e)

To a solution of 2-(4-(((2,4-dimethylbenzoyl)oxy)-methyl-d$_2$)phenyl)acetic acid (3d) (1.9 g, 6.2 mmol) in DCM (40 mL) was added oxalyl chloride (0.79 ml, 7.4 mmol). The mixture was stirred at RT for overnight. The mixture was concentrated to give the crude product of (4-(2-chloro-2-oxoethyl)phenyl)methyl-d$_2$ 2,4-dimethylbenzoate (3e), which was used for next step without further purification.

(R)-(4-(2-(4-benzyl-2-oxooxazolidin-3-yl)-2-oxoethyl)phenyl)methyl-d$_2$ 2,4-dimethylbenzoate (3f)

To a solution of (R)-4-benzyloxazolidin-2-one (1.1 g, 6.2 mmol) in THF (40 mL) at −70° C. was added n-BuLi (1.6 M, 4.3 mL, 6.8 mmol) dropwise, then a solution of (4-(2-chloro-2-oxoethyl)phenyl)methyl-d$_2$ 2,4-dimethylbenzoate (3e) (2.0 g, 6.2 mmol) in THF was added dropwise and the resulting mixture was stirred at −70° C. for 1 h. The reaction was quenched with saturated aqueous NH$_4$Cl solution and extracted with EtOAc (2×50 mL). The extracts were washed with brine, dried over Na$_2$SO$_4$ and concentrated. The residue was purified by column chromatography on silica gel, eluting with PE/EtOAc (10:1~5:1) to give the title compound (R)-(4-(2-(4-benzyl-2-oxooxazolidin-3-yl)-2-oxoethyl)phenyl)methyl-d$_2$ 2,4-dimethyl-benzoate (3f). MS-ESI (m/z): 460 [M+1]$^+$.

(4-((S)-1-((R)-4-benzyl-2-oxooxazolidin-3-yl)-3-((tert-butoxycarbonyl)amino)-1-oxopropan-2-yl)phenyl)methyl-d$_2$ 2,4-dimethylbenzoate (3 g)

To a solution of (R)-(4-(2-(4-benzyl-2-oxooxazolidin-3-yl)-2-oxoethyl)phenyl)-methyl-d$_2$ 2,4-dimethylbenzoate (3f) (1.0 g, 2.2 mmol) in THF (20 mL) at −70° C. was added KHMDS (1.0 M, 2.6 mL, 2.61 mmol) dropwise. The mixture was stirred at −70° C. for 30 min, and then, a solution of tert-butyl ((1H-benzo[d][1,2,3]triazol-1-yl)methyl)carbamate (0.65 g, 2.6 mmol) (WO2017/086941) in THF (3 mL) was added dropwise at −70° C. The mixture was stirred at 0° C. for 1 h. The reaction was quenched with saturated aqueous NH$_4$Cl solution and extracted with EtOAc (3×50 mL). The extracts were washed with brine, dried over Na$_2$SO$_4$ and concentrated. The residue was purified by column chromatography on silica gel, eluting with PE/EtOAc (10:1~5:1) to give the title compound (4-((S)-1-((R)-4-benzyl-2-oxooxazolidin-3-yl)-3-((tert-butoxycarbonyl)amino)-1-oxopropan-2-yl)phenyl)methyl-d$_2$ 2,4-dimethylbenzoate (3 g). MS-ESI (m/z): 589 [M+1]$^+$.

(S)-3-((tert-butoxycarbonyl)amino)-2-(4-(((2,4-dimethylbenzoyl)oxy)methyl-d$_2$)phenyl) propanoic acid (3h)

To a solution of (4-((S)-1-((R)-4-benzyl-2-oxooxazolidin-3-yl)-3-((tert-butoxycarbonyl)amino)-1-oxopropan-2-yl)phenyl)methyl-d$_2$ 2,4-dimethylbenzoate (3 g) (1.1 g, 1.9 mmol) in THF/H$_2$O (22 ml/7 mL) at 0° C. was added H$_2$O$_2$ (30%, 0.85 g, 7.5 mmol) and LiOH.H$_2$O (78 mg, 1.9 mmol) sequentially, The mixture was stirred at 0° C. for 10 min. The reaction was quenched with 10% Na$_2$SO$_3$ aqueous solution. The mixture was extracted with EtOAc (3×50 mL). The extracts were washed with brine, dried over Na$_2$SO$_4$ and concentrated. The residue was purified by column chromatography on silica gel, eluting with DCM/MeOH (100:1~20:1) to give the title compound (S)-3-((tert-butoxycarbonyl)amino)-2-(4-(((2,4-dimethylbenzoyl)oxy)methyl-d$_2$)phenyl)propanoic acid (3h). MS-ESI (m/z): 430 [M+1]$^+$.

(S)-(4-(3-((tert-butoxycarbonyl)amino)-1-(isoquinolin-6-ylamino)-1-oxopropan-2-yl)phenyl)methyl-d$_2$ 2,4-dimethylbenzoate (3i)

To a solution of isoquinolin-6-amine (23 mg, 0.16 mmol) and (S)-3-((tert-butoxycarbonyl)amino)-2-(4-(((2,4-dimethylbenzoyl)oxy)methyl-d$_2$)phenyl)propanoic acid (3h) (43 mg, 0.10 mmol) in DF (1 mL) was added EDCI (39 mg, 0.21 mmol), TEA (33 mg, 0.30 mmol) and HOBT (27 mg, 0.21 mmol). The mixture was stirred at RT for overnight. The mixture was diluted with water and extracted with EtOAc (3×5 mL). The extracts were washed with brine, dried over Na$_2$SO$_4$ and concentrated. The residue was purified by column chromatography on silica gel, eluting with DCM/MeOH (15:1) to give the title compound (S)-(4-(3-((tert-butoxycarbonyl)amino)-1-(isoquinolin-6-ylamino)-1-oxopropan-2-yl)phenyl)methyl-d$_2$ 2,4-dimethylbenzoate (3i). MS-ESI (m/z): 556 [M+1]$^+$.

(S)-(4-(3-amino-1-(isoquinolin-6-ylamino)-1-oxopropan-2-yl)phenyl)methyl-d$_2$ 2,4-dimethylbenzoate (3)

The title compound (S)-(4-(3-amino-1-(isoquinolin-6-ylamino)-1-oxopropan-2-yl)-phenyl)methyl-d$_2$ 2,4-dimethylbenzoate (3) was prepared according to the synthetic method of (S)-4-(3-amino-1-((isoquinolin-6-yl-1-d)amino)-1-oxopropan-2-yl)benzyl 2,4-dimethylbenzoate (1) by replacing (S)-4-(3-((tert-butoxycarbonyl)amino)-1-((isoquinolin-6-yl-1-d)amino)-1-oxopropan-2-yl)benzyl 2,4-dimethylbenzoate (1b) with (S)-(4-(3-((tert-butoxycarbonyl)amino)-1-(isoquinolin-6-ylamino)-1-oxopropan-2-yl)phenyl)methyl-d$_2$ 2,4-dimethylbenzoate (3i). MS-ESI (m/z): 456 [M+1]$^+$.

Example 4

(S)-4-(3-amino-1-((isoquinolin-6-yl-1-d)amino)-1-oxopropan-2-yl-3,3-d$_2$)benzyl 2,4-dimethylbenzoate dihydrochloride (4)

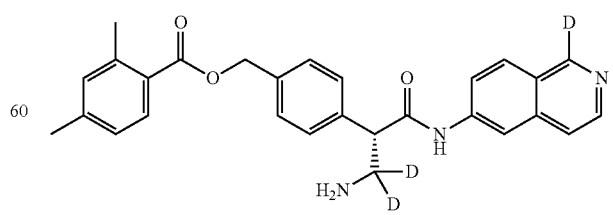

(R)-4-(2-(4-benzyl-2-oxooxazolidin-3-yl)-2-oxo-ethyl)benzyl 2,4-dimethylbenzoate (4a)

The title compound (R)-4-(2-(4-benzyl-2-oxooxazolidin-3-yl)-2-oxoethyl)benzyl 2,4-dimethylbenzoate (4a) was prepared according to the method described in WO2017/086941. MS-ESI (m/z): 458 [M+1]$^+$.

4-((S)-1-((R)-4-benzyl-2-oxooxazolidin-3-yl)-3-((tert-butoxycarbonyl)amino)-1-oxopropan-2-yl-3,3-d2)benzyl 2,4-dimethylbenzoate (4b)

To a solution of the title compound (R)-4-(2-(4-benzyl-2-oxooxazolidin-3-yl)-2-oxoethyl)benzyl 2,4-dimethylbenzoate (4a) (1.0 g, 2.2 mmol) in THF (20 mL) at −70° C. was added KHMDS (1.0 M, 2.6 mL, 2.61 mmol) dropwise. The mixture was stirred at −70° C. for 30 min, and then, a solution of tert-butyl ((1H-benzo[d][1,2,3]triazol-1-yl)methyl-d$_2$)carbamate (F) (0.65 g, 2.6 mmol) in THF (3 mL) was added dropwise at −70° C. The mixture was stirred at 0° C. for 1 h. The reaction was quenched with saturated aqueous NH$_4$Cl solution and extracted with EtOAc (3×50 mL). The extracts were washed with brine, dried over Na$_2$SO$_4$ and concentrated. The residue was purified by column chromatography on silica gel, eluting with PE/EtOAc (10:1~5:1) to give the title compound 4-((S)-1-((R)-4-benzyl-2-oxooxazolidin-3-yl)-3-((tert-butoxycarbonyl)amino)-1-oxopropan-2-yl-3,3-d$_2$)benzyl 2,4-dimethylbenzoate (4b). MS-ESI (m/z): 589 [M+1]$^+$.

(S)-3-((tert-butoxycarbonyl)amino)-2-(4-(((2,4-dimethylbenzoyl)oxy)methyl)phenyl)propanoic-3,3-d2 acid (4c)

The title compound (S)-3-((tert-butoxycarbonyl)amino)-2-(4-(((2,4-dimethyl-benzoyl)oxy)methyl)phenyl)propanoic-3,3-d$_2$ acid (4c) was prepared according to the synthetic method of (S)-3-((tert-butoxycarbonyl)amino)-2-(4-(((2,4-dimethylbenzoyl)oxy)methyl-d$_2$)-phenyl)propanoic acid (3h) by replacing (4-((S)-1-((R)-4-benzyl-2-oxooxazolidin-3-yl)-3-((tert-butoxycarbonyl)amino)-1-oxopropan-2-yl)phenyl)methyl-d$_2$ 2,4-dimethylbenzoate (3 g) with 4-((S)-1-((R)-4-benzyl-2-oxooxazolidin-3-yl)-3-((tert-butoxycarbonyl)amino)-1-oxopropan-2-yl-3,3-d$_2$)benzyl 2,4-dimethylbenzoate (4b). MS-ESI (m/z): 430 [M+1]$^+$

(S)-4-(3-amino-1-((isoquinolin-6-yl-1-d)amino)-1-oxopropan-2-yl-3,3-d2)benzyl 2,4-dimethylbenzoate (4d)

The title compound (S)-4-(3-amino-1-((isoquinolin-6-yl-1-d)amino)-1-oxopropan-2-yl-3,3-d$_2$)benzyl 2,4-dimethylbenzoate (4d) was prepared according to the synthetic method of (S)-4-(3-amino-1-((isoquinolin-6-yl-1-d)amino)-1-oxopropan-2-yl)benzyl 2,4-dimethylbenzoate (1) by replacing (S)-3-((tert-butoxycarbonyl)amino)-2-(4-(((2,4-dimethyl-benzoyl)oxy)methyl) phenyl)propanoic acid (1a) with (S)-3-((tert-butoxycarbonyl)amino)-2-(4-(((2,4-dimethylbenzoyl) oxy)methyl)phenyl)propanoic-3,3-d$_2$ acid (4c). MS-ESI (m/z): 457 [M+1]$^+$.

(S)-4-(3-amino-1-((isoquinolin-6-yl-1-d)amino)-1-oxopropan-2-yl-3,3-d$_2$)benzyl 2,4-dimethylbenzoate dihydrochloride (4)

To a solution of (S)-4-(3-amino-1-((isoquinolin-6-yl-1-d)amino)-1-oxopropan-2-yl-3,3-d$_2$)benzyl 2,4-dimethylbenzoate (4d) (22 mg, 0.048 mmol) in DCM (1 mL) and MeOH (0.1 mL) was added HCl (30% EtOH solution, 0.108 mmol). After being stirred for 10 min, the mixture was concentrated to give the title compound (S)-4-(3-amino-1-((isoquinolin-6-yl-1-d)amino)-1-oxopropan-2-yl-3,3-d$_2$)benzyl 2,4-dimethylbenzoate dihydrochloride (4). MS-ESI (m/z): 457 [M+1]$^+$.

Example 5

(S)-(4-(3-amino-1-(isoquinolin-6-ylamino)-1-oxo-propan-2-yl-2,3,3-d)phenyl)-methyl-d$_2$ 2,4-bis(methyl-d$_3$)benzoate dihydrochloride (5)

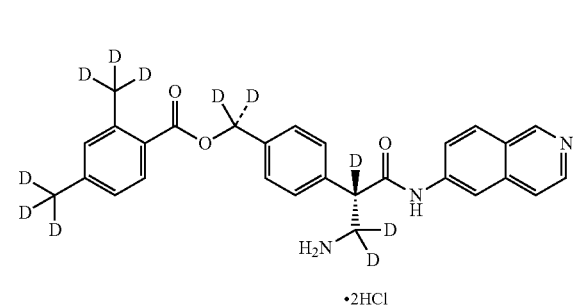

(4-(2-Methoxy-2-oxoethyl-1,1-d2)phenyl)methyl-d$_2$2,4-bis(methyl-d$_3$)benzoate (5a)

A mixture of methyl 2-(4-(hydroxymethyl-d$_2$)phenyl)acetate-d$_2$ (E) (610 mg, 3.30 mmol), 2,4-bis(methyl-d$_3$)benzoic acid (C) (517 mg, 3.30 mmol), EDCI (1.2 g, 6.0 mmol) and DMAP (81 mg, 0.66 mmol) in DCM (20 mL) was stirred at RT for overnight. The mixture was diluted with DCM and washed with H$_2$O and brine, dried over Na$_2$SO$_4$ and concentrated. The residue was purified by column chromatography on silica gel, eluting with PE/EtOAc (10:1) to give the title compound (4-(2-methoxy-2-oxoethyl-1,1-d$_2$)phenyl)methyl-d$_2$ 2,4-bis(methyl-d$_3$) benzoate (5a). MS-ESI (m/z): 323 [M+1]$^+$.

2-(4-(((2,4-Bis(methyl-d$_3$)benzoyl)oxy)methyl-d$_2$)phenyl)acetic-2,2-d$_2$ acid (5b)

To a solution of (4-(2-methoxy-2-oxoethyl-1,1-d$_2$)phenyl)methyl-d$_2$ 2,4-bis(methyl-d$_3$)benzoate (5a) (752 mg, 2.33 mmol) in D$_2$O (15 mL) and THF (10 mL) was added LiOH.H$_2$O (108 mg, 2.6 mmol). The mixture was stirred at RT for 2 h. The mixture was acidified to pH=2~3, diluted with H$_2$O and extracted with EtOAc (3×). The combined EtOAc phase was washed with H$_2$O and brine, dried over Na$_2$SO$_4$ and concentrated to give the title compound 2-(4-(((2,4-bis(methyl-d$_3$)benzoyl)oxy)methyl-d$_2$)phenyl)acetic-2,2-d$_2$ acid (5b). MS-ESI (m/z): 307 [M−1]$^−$.

(R)-(4-(2-(4-benzyl-2-oxooxazolidin-3-yl)-2-oxo-ethyl-1,1-$d_2$)phenyl)methyl-$d_2$ 2,4-bis(methyl-$d_3$) benzoate (5c)

The title compound (R)-(4-(2-(4-benzyl-2-oxooxazolidin-3-yl)-2-oxoethyl-1,1-$d_2$)-phenyl)methyl-$d_2$ 2,4-bis(methyl-$d_3$)benzoate (5c) was prepared according to the synthetic method of 3f by replacing 2-(4-(((2,4-dimethylbenzoyl)oxy)-methyl-$d_2$)phenyl)acetic acid (3d) with 2-(4-(((2,4-bis(methyl-$d_3$)benzoyl)oxy)methyl-$d_2$)phenyl)acetic-2,2-$d_2$ acid (5b). MS-ESI (m/z): 468 [M+1]$^+$.

(S)-(4-(1-((R)-4-benzyl-2-oxooxazolidin-3-yl)-3-((tert-butoxycarbonyl)amino)-1-oxopropan-2-yl-2,3,3-$d_3$)phenyl)methyl-$d_2$ 2,4-bis(methyl-$d_3$)benzoate (5d)

The title compound (S)-(4-(1-((R)-4-benzyl-2-oxooxazolidin-3-yl)-3-((tert-butoxycarbonyl)amino)-1-oxopropan-2-yl-2,3,3-$d_3$)phenyl)methyl-$d_2$ 2,4-bis(methyl-$d_3$)benzoate (5d) was prepared according to the synthetic method of 3 g by replacing (R)-(4-(2-(4-benzyl-2-oxooxazolidin-3-yl)-2-oxoethyl)phenyl)-methyl-$d_2$ 2,4-dimethylbenzoate (3f) and tert-butyl ((1H-benzo[d][1,2,3]triazol-1-yl)methyl)carbamate with (R)-(4-(2-(4-benzyl-2-oxooxazolidin-3-yl)-2-oxoethyl-1,1-$d_2$)phenyl)methyl-$d_2$ 2,4-bis(methyl-$d_3$)benzoate (5c) and tert-butyl ((1H-benzo[d][1,2,3]triazol-1-yl)methyl-$d_2$)carbamate (F). MS-ESI (m/z): 598 [M+1]$^+$.

(S)-2-(4-(((2,4-bis(methyl-$d_3$)benzoyl)oxy)methyl-d2)phenyl)-3-((tert-butoxycarbonyl)amino)propanoic-2,3,3-$d_3$ acid (5e)

To a solution of (S)-(4-(1-((R)-4-benzyl-2-oxooxazolidin-3-yl)-3-((tert-butoxycarbonyl)amino)-1-oxopropan-2-yl-2,3,3-$d_3$)phenyl)methyl-$d_2$ 2,4-bis(methyl-$d_3$)benzoate (5d) (538 mg, 0.904 mmol) in $D_2O$ (5 mL) and THF (10 mL) at 0° C. was added $H_2O_2$ (0.41 ml, 3.61 mmol) followed by LiOH.$H_2O$ (42 mg, 0.99 mmol). The mixture was stirred at 0° C. for 0.5 h, then quenched with $NaHSO_3$ (10% aqueous solution). The mixture was acidified to pH=2~3 and extracted with EtOAc (3×50 mL). The extracts were washed with brine, dried over $Na_2SO_4$, and concentrated. The residue was purified by column chromatography on silica gel, eluting with DCM/MeOH (100:1~10:1) to give the title compound (S)-2-(4-(((2,4-bis(methyl-$d_3$)benzoyl)oxy)-methyl-$d_2$)phenyl)-3-((tert-butoxycarbonyl)amino)propanoic-2,3,3-$d_3$ acid (5e). MS-ESI (m/z): 439 [M−1]$^−$.

(S)-(4-(3-amino-1-(isoquinolin-6-ylamino)-1-oxopropan-2-yl-2,3,3-$d_3$)phenyl)methyl-$d_2$ 2,4-bis(methyl-$d_3$)benzoate (5f)

The title compound (S)-(4-(3-amino-1-(isoquinolin-6-ylamino)-1-oxopropan-2-yl-2,3,3-$d_3$)phenyl)methyl-$d_2$ 2,4-bis(methyl-$d_3$)benzoate (5f) was prepared according to the synthetic method of 3 by replacing (S)-3-((tert-butoxycarbonyl)amino)-2-(4-(((2,4-dimethylbenzoyl)oxy)methyl-$d_2$)phenyl) propanoic acid (3h) with (S)-2-(4-(((2,4-bis(methyl-$d_3$)benzoyl)oxy)methyl-$d_2$)phenyl)-3-((tert-butoxycarbonyl)amino)propanoic-2,3,3-$d_3$ acid (5e). MS-ESI (m/z): 465 [M+1]$^+$.

(S)-(4-(3-amino-1-(isoquinolin-6-ylamino)-1-oxopropan-2-yl-2,3,3-d3)phenyl)methyl-$d_2$ 2,4-bis(methyl-$d_3$)benzoate dihydrochloride (5)

To a solution of (S)-(4-(3-amino-1-(isoquinolin-6-ylamino)-1-oxopropan-2-yl-2,3,3-d)phenyl)methyl-$d_2$ 2,4-bis(methyl-$d_3$)benzoate (5f) (20 mg, 0.043 mmol) in DCM (1 mL) and MeOH (0.1 mL) was added HCl (30% EtOH solution, 0.108 mmol). After being stirred for 10 min, the mixture was concentrated to give the title compound (S)-(4-(3-amino-1-(isoquinolin-6-ylamino)-1-oxopropan-2-yl-2,3,3-$d_3$)phenyl)methyl-$d_2$ 2,4-bis(methyl-$d_3$)benzoate dihydrochloride (5). MS-ESI (m/z): 465 [M+1]$^+$.

Example 6

(S)-(4-(3-amino-1-(isoquinolin-6-ylamino)-1-oxopropan-2-yl-2-d)phenyl)methyl-$d_2$ 2,4-bis(methyl-$d_3$)benzoate dihydrochloride (6)

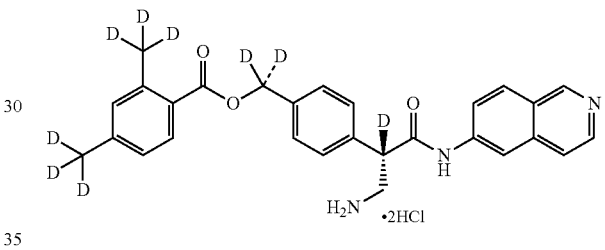

6

The title compound (S)-(4-(3-amino-1-(isoquinolin-6-ylamino)-1-oxopropan-2-yl-2-d)phenyl)methyl-$d_2$ 2,4-bis(methyl-$d_3$)benzoate dihydrochloride (6) was prepared according to the synthetic method of 5 by replacing tert-butyl ((1H-benzo[d][1,2,3]triazol-1-yl)methyl-$d_2$)carbamate (F) with tert-butyl ((1H-benzo[d][1,2,3]triazol-1-yl)methyl) carbamate. MS-ESI (m/z): 463 [M+1]$^+$.

Reference Compound 1

(S)-4-(3-amino-1-(isoquinolin-6-ylamino)-1-oxopropan-2-yl)benzyl 2,4-dimethylbenzoate dihydrochloride (Reference compound 1)

(S)-4-(3-amino-1-(isoquinolin-6-ylamino)-1-oxopropan-2-yl)benzyl 2,4-dimethylbenzoate was disclosed and prepared following essentially the same procedures outlined on pages 21 of WO2017/086941. Reference compound 1 was prepared according to the synthetic method of (5) by replacing(S)-(4-(3-amino-1-(isoquinolin-6-ylamino)-1-oxopropan-2-yl-2,3,3-$d_3$)phenyl)methyl-$d_2$ 2,4-bis(methyl-$d_3$)benzoate (5f) with (S)-4-(3-amino-1-(isoquinolin-6-ylamino)-1-oxopropan-2-yl)benzyl 2,4-dimethylbenzoate.

Following essentially the same procedures described for Examples 1-6, Examples 7-24 listed in Table 1 were prepared from the appropriate starting materials which are commercially available or known in the literature. The structures and names of Examples 7-24 are given in Table 1.

TABLE 1

| EXAMPLE | STRUCTURE | NAME | DATA |
|---|---|---|---|
| 7 | 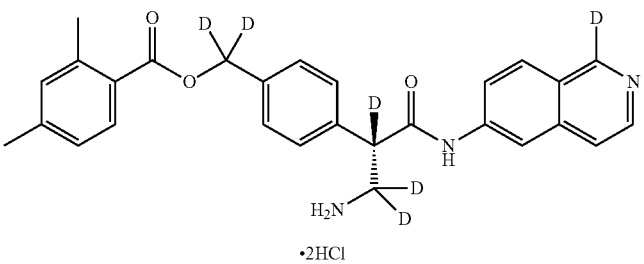 •2HCl | (S)-(4-(3-amino-1-((isoquinolin-6-yl-1-d)amino)-1-oxopropan-2-yl-2,3,3-d₃)phenyl)methyl-d₂ 2,4-dimethylbenzoate dihydrochloride | MS-ESI (m/z): 460 [M + 1]⁺ |
| 8 | 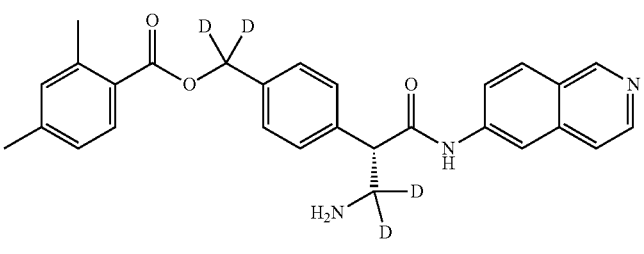 •2HCl | (S)-(4-(3-amino-1-(isoquinolin-6-ylamino)-1-oxopropan-2-yl-3,3-d₂)phenyl)methyl-d₂ 2,4-dimethylbenzoate dihydrochloride | MS-ESI (m/z): 458 [M + 1]⁺ |
| 9 | 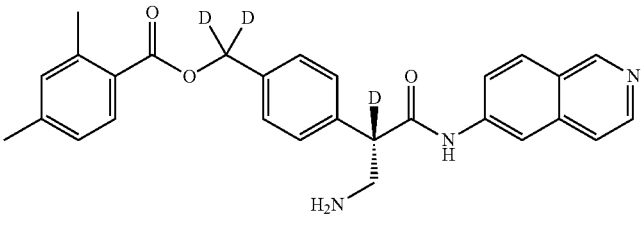 •2HCl | (S)-(4-(3-amino-1-(isoquinolin-6-ylamino)-1-oxopropan-2-yl-2-d)phenyl)methyl-d₂ 2,4-dimethylbenzoate dihydrochloride | MS-ESI (m/z): 457 [M + 1]⁺ |
| 10 | 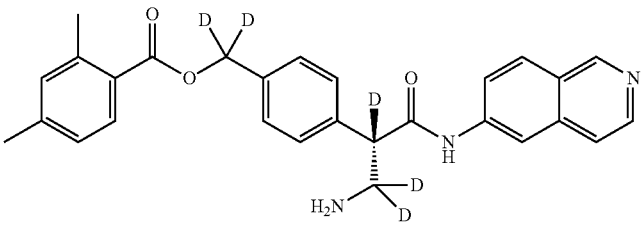 •2HCl | (S)-(4-(3-amino-1-(isoquinolin-6-ylamino)-1-oxopropan-2-yl-2,3,3-d₃)phenyl)methyl-d₂ 2,4-dimethylbenzoate dihydrochloride | MS-ESI (m/z): 459 [M + 1]⁺ |
| 11 | 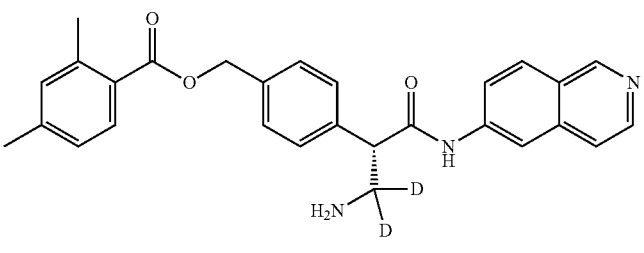 •2HCl | (S)-4-(3-amino-1-(isoquinolin-6-ylamino)-1-oxopropan-2-yl-3,3-d₂)benzyl 2,4-dimethylbenzoate dihydrochloride | MS-ESI (m/z): 456 [M + 1]⁺ |

TABLE 1-continued

| EXAMPLE | STRUCTURE | NAME | DATA |
|---|---|---|---|
| 12 | 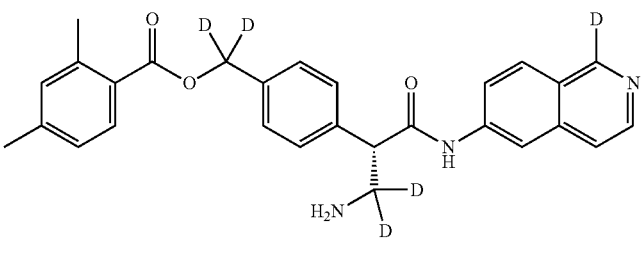 •2HCl | (S)-(4-(3-amino-1-((isoquinolin-6-yl-1-d)amino)-1-oxopropan-2-yl-3,3-d₂)phenyl)methyl-d₂ 2,4-dimethylbenzoate dihydrochloride | MS-ESI (m/z): 459 [M + 1]⁺ |
| 13 | 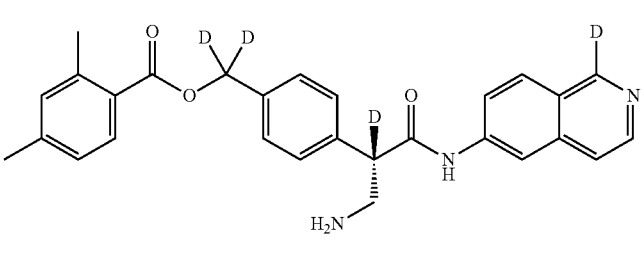 •2HCl | (S)-(4-(3-amino-1-((isoquinolin-6-yl-1-d)amino)-1-oxopropan-2-yl-2-d)phenyl)methyl-d₂ 2,4-dimethylbenzoate dihydrochloride | MS-ESI (m/z): 458 [M + 1]⁺ |
| 14 | 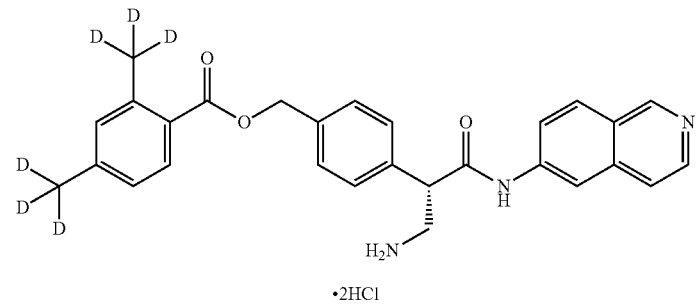 [SMILES: [2H]C([2H])([2H])c1ccc(C(=O)OCc2ccc([C@@H](CN)C(=O)Nc3ccc4cnccc4c3)cc2)c(C([2H])([2H])[2H])c1] •2HCl | (S)-4-(3-amino-1-(isoquinolin-6-ylamino)-1-oxopropan-2-yl)benzyl 2,4-bis(methyl-d₃)benzoate dihydrochloride | MS-ESI (m/z): 460 [M + 1]⁺ |
| 15 | 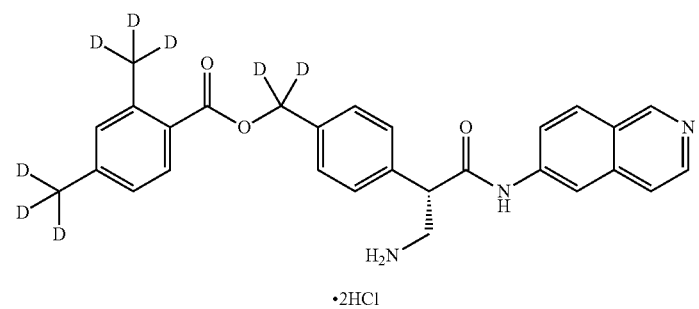 [SMILES: [2H]C([2H])([2H])c1ccc(C(=O)OC([2H])([2H])c2ccc([C@@H](CN)C(=O)Nc3ccc4cnccc4c3)cc2)c(C([2H])([2H])[2H])c1] •2HCl | (S)-(4-(3-amino-1-(isoquinolin-6-ylamino)-1-oxopropan-2-yl)phenyl)methyl-d₂ 2,4-bis(methyl-d₃)benzoate dihydrochloride | MS-ESI (m/z): 462 [M + 1]⁺ |
| 16 | 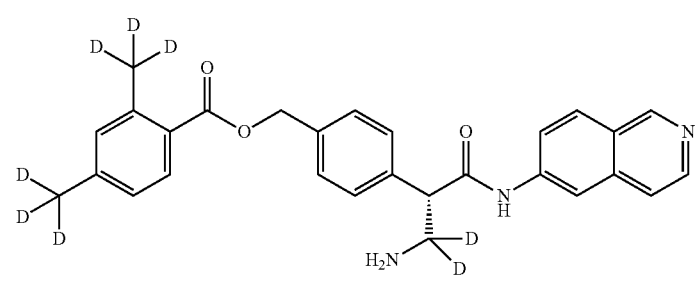 •2HCl | (S)-4-(3-amino-1-(isoquinolin-6-ylamino)-1-oxopropan-2-yl-3,3-d₂)benzyl 2,4-bis(methyl-d₃)benzoate dihydrochloride | MS-ESI (m/z): 462 [M + 1]⁺ |

TABLE 1-continued

| EXAMPLE | STRUCTURE | NAME | DATA |
|---|---|---|---|
| 17 | 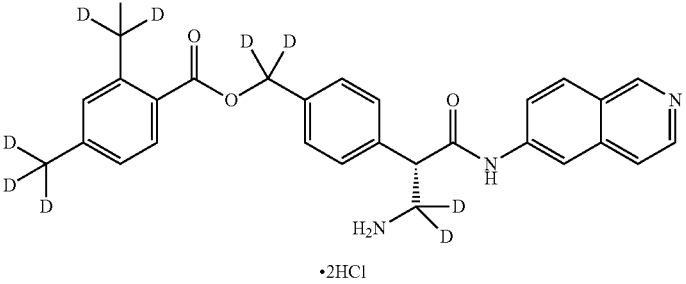 | (S)-(4-(3-amino-1-(isoquinolin-6-ylamino)-1-oxopropan-2-yl-3,3-$d_2$)phenyl)methyl-$d_2$ 2,4-bis(methyl-$d_3$)benzoate dihydrochloride | MS-ESI (m/z): 464 [M + 1]$^+$ |
| 18 | 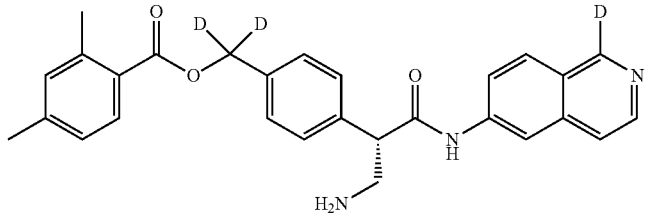 [SMILES: [2H]c1nccc2cc(NC(=O)[C@H](CN)c3ccc(C([2H])([2H])OC(=O)c4ccc(C)cc4C)cc3)ccc12] | (S)-(4-(3-amino-1-((isoquinolin-6-yl-1-d)amino)-1-oxopropan-2-yl)phenyl)methyl-$d_2$ 2,4-dimethylbenzoate | MS-ESI (m/z): 457 [M + 1]$^+$ |
| 19 | 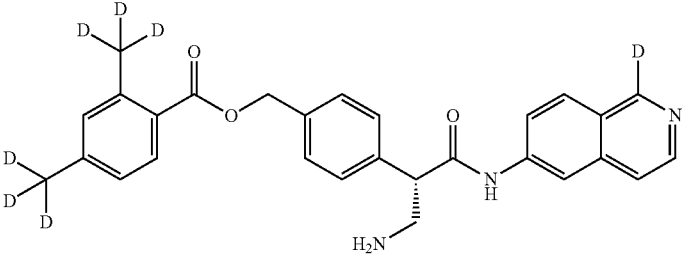 | (S)-4-(3-amino-1-((isoquinolin-6-yl-1-d)amino)-1-oxopropan-2-yl)benzyl 2,4-bis(methyl-$d_3$)benzoate dihydrochloride | MS-ESI (m/z): 461 [M + 1]$^+$ |
| 20 | 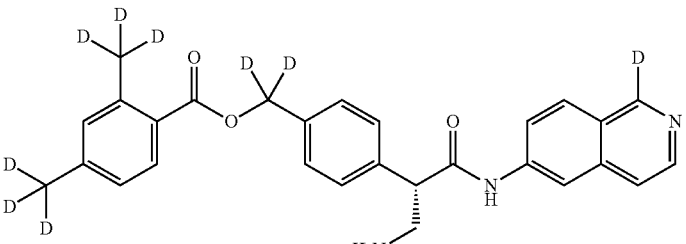 | (S)-(4-(3-amino-1-((isoquinolin-6-yl-1-d)amino)-1-oxopropan-2-yl)phenyl)methyl-$d_2$ 2,4-bis(methyl-$d_3$)benzoate dihydrochloride | MS-ESI (m/z): 463 [M + 1]$^+$ |
| 21 | 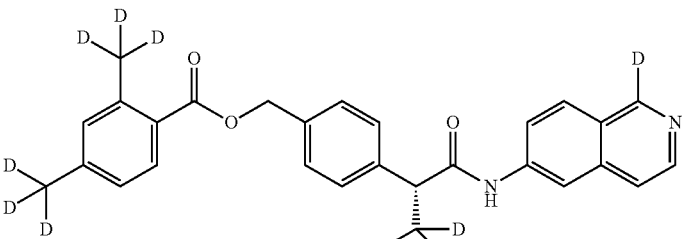 | (S)-4-(3-amino-1-((isoquinolin-6-yl-1-d)amino)-1-oxopropan-2-yl-3,3-$d_2$)benzyl 2,4-bis(methyl-$d_3$)benzoate dihydrochloride | MS-ESI (m/z): 463 [M + 1]$^+$ |

TABLE 1-continued

| EXAMPLE | STRUCTURE | NAME | DATA |
|---|---|---|---|
| 22 | 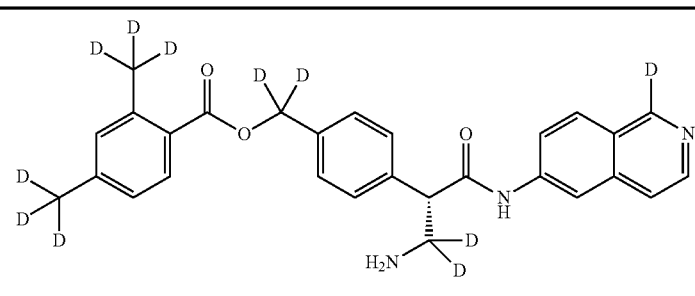 •2HCl | (S)-(4-(3-amino-1-((isoquinolin-6-yl-1-d)amino)-1-oxopropan-2-yl-3,3-$d_2$)phenyl)methyl-$d_2$ 2,4-bis(methyl-$d_3$)benzoate dihydrochloride | MS-ESI (m/z): 465 [M + 1]$^+$ |
| 23 | 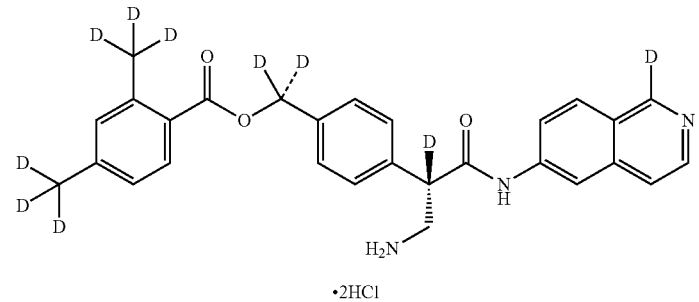 •2HCl | (S)-(4-(3-amino-1-((isoquinolin-6-yl-1-d)amino)-1-oxopropan-2-yl-2-d)phenyl)methyl-$d_2$ 2,4-bis(methyl-$d_3$)benzoate dihydrochloride | MS-ESI (m/z): 464 [M + 1]$^+$ |
| 24 | 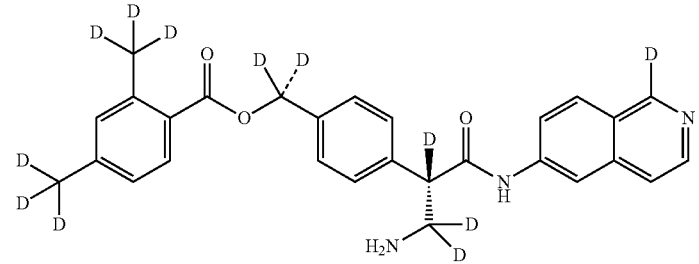 •2HCl | (S)-(4-(3-amino-1-((isoquinolin-6-yl-1-d)amino)-1-oxopropan-2-yl-2,3,3-$d_3$)phenyl)methyl-$d_2$ 2,4-bis(methyl-$d_3$)benzoate dihydrochloride | MS-ESI (m/z): 466 [M + 1]$^+$ |

Cell Proliferation Assays

ROCK-I(h) In Vitro Inhibition Activity-Method A

ROCK-I(h) kinase assays were conducted using the KinaseProfiler™ service of Eurofins Pharma Discovery Services UK Limited. ROCK-I(h) was incubated with the test compound in assay buffer containing 8 mM MOPS pH 7.0 (VWR cat #441644J) 0.2 mM EDTA (Sigma cat #E5134), 30 μM KEAKEKRQEQIAKRRRLSSLRASTSKSGGSQK (Pepceuticals), 10 mM magnesium acetate (Merck Millipore cat #105819) and [γ-33P-ATP] (Perkin Elmer cat #NEG602K). Test compound in 100% DMSO (Calbiochem cat #317275) was spotted into a 96-well assay plate prior using a Mosquito X1 (TTP Labtech) prior to addition of the reaction mix. The reaction was initiated by the addition of the Mg/ATP mix using a Matrix Wellmate. After incubation for 40 minutes at room temperature, the reaction was stopped by the addition of a 3% phosphoric acid solution (Fisher Scientific cat #O/0500/PB17) using a Matrix Wellmate. An aliquot of the reaction was then spotted onto a filtermat and washed in phosphoric acid followed by a rinse in methanol prior to drying and scintillation counting in a Trilux Wallac Microbeta detector (Perkin Elmer). Results were expressed in relation to controls containing DMSO only in place of test compound. Where applicable, IC50 curve analysis was performed using XLFit version 5.3 (ID Business Solutions). Sigmoidal dose-response (variable slope) curves are fitted using non-linear regression analysis.

ROCK-II(h) kinase assays were conducted using the KinaseProfiler™ service of Eurofins Pharma Discovery Services UK Limited. ROCK-II(h) was incubated with the test compound in assay buffer containing 50 mM Tris pH 7.5 (VWR cat #103157P), 0.1 mM EGTA (VWR cat #20308), 30 μM KEAKEKRQEQIAKRRRLSSLRASTSKSGGSQK (Pepceuticals), 10 mM magnesium acetate and [γ-33P-ATP] (Perkin Elmer cat #NEG602K). Test compound in 100% DMSO (Calbiochem cat #317275) was spotted into a 96-well assay plate prior using a Mosquito X1 (TTP Labtech) prior to addition of the reaction mix. The reaction was initiated by the addition of the Mg/ATP mix using a Matrix Wellmate. After incubation for 40 minutes at room temperature, the reaction was stopped by the addition of a 3% phosphoric acid solution (Fisher Scientific cat #O/0500/PB17) using a Matrix Wellmate. An aliquot of the reaction was then spotted onto a filtermat and washed in phosphoric acid followed by a rinse in methanol prior to drying and scintillation counting in a Trilux Wallac Microbeta detector (Perkin Elmer). Results were expressed in relation to controls containing DMSO only in place of test compound. Where applicable, IC$_{50}$ curve analysis was performed using XLFit version 5.3 (ID Business Solutions). Sigmoidal dose-response (variable slope) curves are fitted using non-linear regression analysis.

Select compounds prepared as described above were assayed according to the biological procedures described in Method A. The results are given in the table 2.

TABLE 2

| Example | ROCK-I (h) IC$_{50}$ (nM) | ROCK-II (h) IC$_{50}$ (nM) |
|---|---|---|
| 1 | 44 | 15 |
| 3 | 64 | 18 |
| 18 | 26 | 8 |

ROCK-I(h) In Vitro Inhibition Activity-Method B

ROCK-I (Invitrogen, PV3691) kinase assays were conducted using the HTRF® KinEASE-STK kit service of CISBIO. Transfer 10 nl compound dilutions into each well of assay plates (784075, Greiner) using Echo 550; Centrifuge compound plates at 1000 g for 1 min. Seal the assay plate. Prepare 5×ROCK-I (Invitrogen, PV3691) in 1× kinase buffer (1 volume of enzymatic buffer 5× with 4 volumes of distilled water; 5 mM MgCl$_2$; 1 mM DTT). Add 2 μl of 5× ROCK-I into 384-well assay plate (784075, Greiner). Add 4 μl× kinase buffer into each well of the assay plate and centrifuge plates at 1000 g for 30 s, RT for 10 min. Prepare 5× TK-substrate-biotin (5 μM) in kinase buffer and 5×ATP (100 μM) in kinase buffer. Start the reaction by adding 2 μl STK-substrate-biotin and 2 μl ATP. Centrifuge plates at 1000 g for 30 s. Seal the assay plate, RT for 20 min. Prepare 4× Sa-XL 665 (250 nM) and TK-antibody-Cryptate in HTRF detection buffer. Add 5 μl Sa-XL 665 and 5 μl TK-antibody-Cryptate into each well of the assay plate. Centrifuge plate at 1000 g for 30 s, RT for 1 h. Read fluorescence signal at 615 nm (Cryptate) and 665 nm (XL665) on Envision 2104 plate reader (Perkin Elmer). A Ratio (665/615 nm) is calculated for each well. Calculate IC$_{50}$ by fitting % Inhibition values and log of compound concentrations to nonlinear regression (dose response–variable slope) with GraphPad 6.0.

Select compounds prepared as described above were assayed according to the biological procedures described in Method B. The results are given in the table 3.

TABLE 3

| Example | ROCK-I (h) IC$_{50}$ (nM) |
|---|---|
| 4 | 14 |
| 5 | 39 |
| 6 | 21 |
| 7 | 27 |
| 8 | 23 |
| 9 | 21 |
| 10 | 17 |
| 11 | 21 |
| 12 | 15 |
| 13 | 17 |
| 14 | 19 |
| 15 | 27 |
| 16 | 19 |
| 17 | 21 |
| 19 | 26 |
| 20 | 19 |
| 21 | 20 |

TABLE 3-continued

| Example | ROCK-I (h) IC$_{50}$ (nM) |
|---|---|
| 22 | 33 |
| 23 | 18 |
| Reference compound 1 | 18 |

ROCK In Vivo Inhibition Activity-Method C

Oxybuprocaine (Santen Co. JP lot: B2031); Carbonate restrainer (harvard apparatus); TONOVET Plus (Finland icare); Chinchilla rabbits: 2~8 months of age and 2.23~4.41 kg of body weight (Dongfang Breeding Co., Ltd., Pizhou, Licence: SCXK (su) 2014-0005, Certificate No.: 201814493, 201826314).

Eighteen male rabbits were randomly assigned to 3 groups (6 animals/group). Vehicle control, Rhopressa® (0.02% netarsudil, equivalent to 0.2 mg/ml netarsudil), or 0.2 mg/mL Example 11 were topically administered to right eye (30 μL/eye/dose) once daily for 3 days, with the fellow left eye treated with saline as the internal control. Clinical observations and ophthalmic examinations were performed once daily. IOP was measured by TONOVET Plus before first dosing, and at 0.5, 2, 4, 6 and 24 h after each first dosing on day 1 and day 3.

The change of IOP % was calculated using the following formula:

$$\text{The change of IOP \%}(\Delta \text{IOP \%}) = [\text{IOP(time)} - \text{IOP(control)}]/\text{IOP(control)} * 100).$$

Select compounds prepared as described above were assayed according to the biological procedures described in Method C. The results of dosing on day 3 at 24 h are given in the table 4.

TABLE 4

| Example | ΔIOP % |
|---|---|
| 1 | −1.5 |
| 3 | −5.02 |
| 4 | −15.63 |
| 5 | 1.19 |
| 6 | −16.08 |
| 7 | 0.48 |
| 8 | −7.52 |
| 9 | −3.06 |
| 10 | −0.78 |
| 11 | −9.57 |
| 12 | −5.23 |
| 13 | −8.48 |
| 14 | −5.81 |
| 15 | −4.25 |
| 16 | −1.44 |
| 18 | −1.1 |
| 19 | −3.3 |
| 20 | −4.89 |
| 21 | −5.06 |
| 22 | 0.08 |
| 23 | −0.87 |
| Reference compound 1 | −4.35 |

What is claimed is:

1. A compound of formula (I):

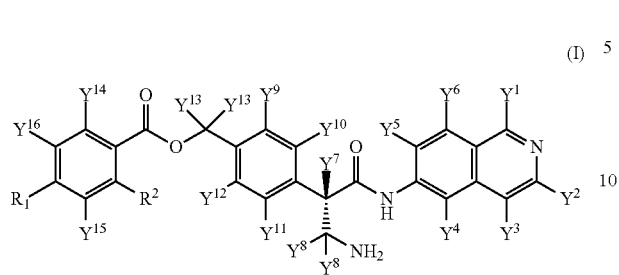

(I)

or a pharmaceutically acceptable salt thereof, wherein
$R^1$ is selected from $CH_3$, $CH_2D$, $CHD_2$ and $CD_3$;
$R^2$ is selected from $CH_3$, $CH_2D$, $CHD_2$ and $CD_3$;
$Y^1, Y^2, Y^3, Y^4, Y^5, Y^6, Y^7, Y^9, Y^{10}, Y^{11}, Y^{12}, Y^{14}, Y^{15}$ and $Y^{16}$ are each independently selected from hydrogen and deuterium;
each $Y^8$ is independently selected from hydrogen and deuterium, provided that both $Y^8$ are the same;
each $Y^{13}$ is independently selected from hydrogen and deuterium, provided that both $Y^{13}$ are the same;
provided that the compound of formula (I) contains at least one deuterium atom.

2. The compound of claim 1 or the pharmaceutically acceptable salt thereof, wherein $Y^1$ is deuterium.

3. The compound of claim 1 or the pharmaceutically acceptable salt thereof, wherein $Y^2$ is deuterium.

4. The compound of claim 1 or the pharmaceutically acceptable salt thereof, wherein $Y^3$ is deuterium.

5. The compound of claim 1 or the pharmaceutically acceptable salt thereof, wherein $Y^7$ is deuterium.

6. The compound of claim 1 or the pharmaceutically acceptable salt thereof, wherein both $Y^8$ are deuterium.

7. The compound of claim 1 or the pharmaceutically acceptable salt thereof, wherein both $Y^{13}$ are deuterium.

8. The compound of claim 1 or the pharmaceutically acceptable salt thereof, wherein $R^1$ is selected from $CH_3$ and $CD_3$.

9. The compound of claim 1 or the pharmaceutically acceptable salt thereof, wherein $R^2$ is selected from $CH_3$ and $CD_3$.

10. The compound of claim 1, selected from

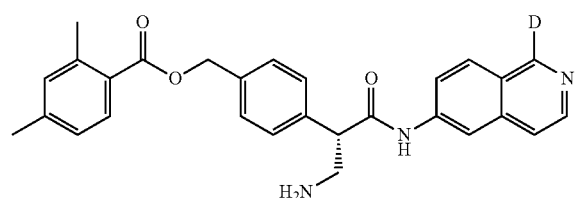

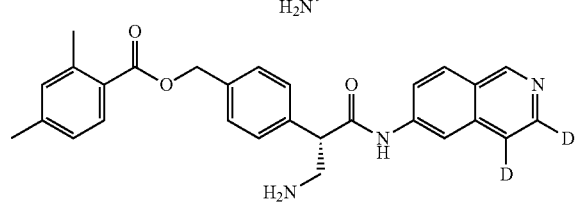

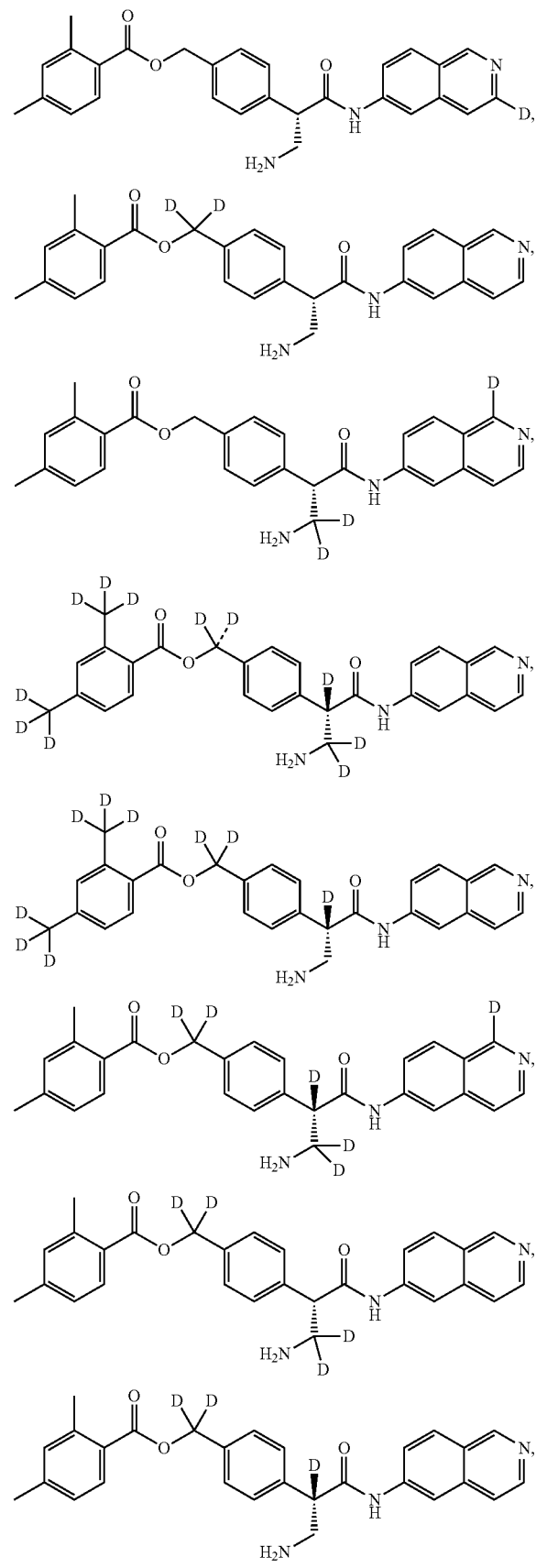

-continued and pharmaceutically acceptable salts thereof.

11. The compound of claim 10 or the pharmaceutically acceptable salt thereof, selected from

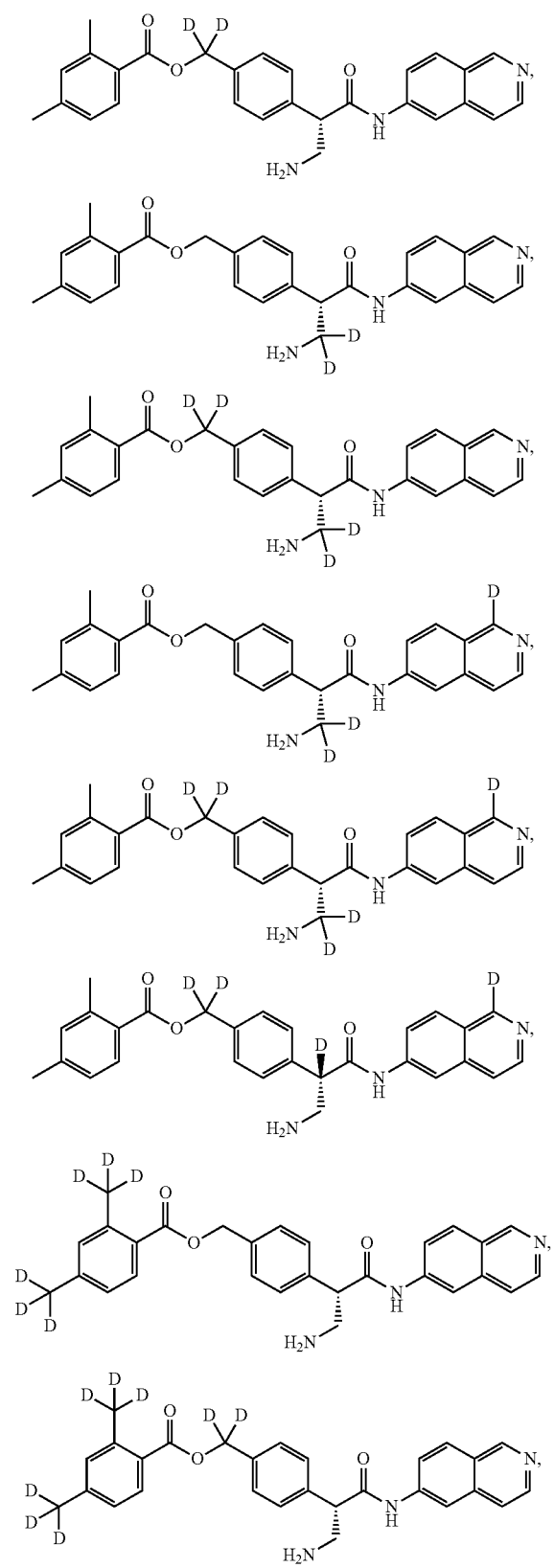

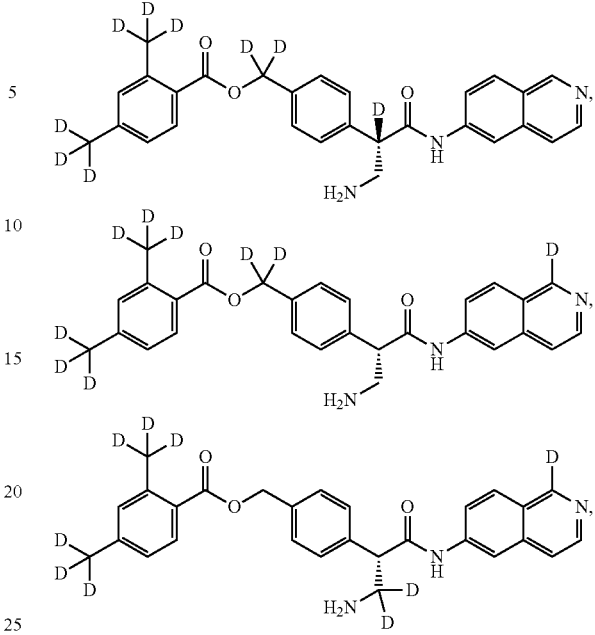

and pharmaceutically acceptable salts thereof.

12. The compound of claim 11 or the pharmaceutically acceptable salt thereof, selected from

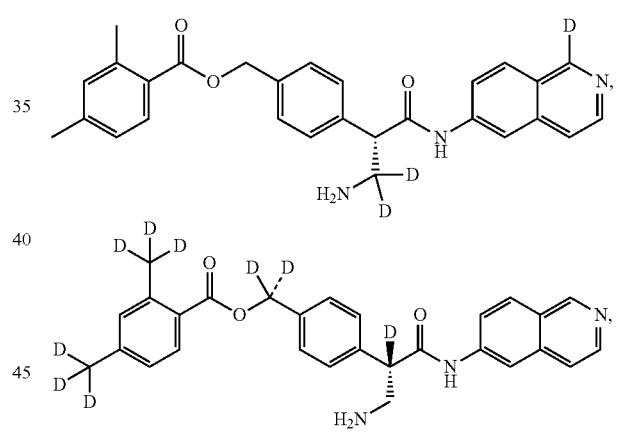

and pharmaceutically acceptable salts thereof.

13. The compound of claim 1 or the pharmaceutically acceptable salt thereof, wherein the pharmaceutically acceptable salt thereof is hydrochloride.

14. The compound of claim 13 or the pharmaceutically acceptable salt thereof, wherein the pharmaceutically acceptable salt thereof is dihydrochloride.

15. A pharmaceutical composition, comprising the compound of claim 1 or the pharmaceutically acceptable salt thereof and at least one pharmaceutically acceptable carrier.

16. A method of treating, ameliorating or preventing a condition, which responds to inhibition of ROCK, comprising administering to a subject in need of such treatment an effective amount of the compound of claim 1, or the pharmaceutically acceptable salt thereof, or the pharmaceutical composition thereof, and optionally in combination with a second therapeutic agent.

17. A method of treating elevate intraocular pressure, comprising administering to a subject in need of such treatment an effective amount of the compound of claim 1 or the pharmaceutically acceptable salt thereof.

18. A pharmaceutical composition, comprising the compound of claim 10 or the pharmaceutically acceptable salt thereof and at least one pharmaceutically acceptable carrier.

19. A method of treating, ameliorating or preventing a condition, which responds to inhibition of ROCK, comprising administering to a subject in need of such treatment an effective amount of the compound of claim 10, or the pharmaceutically acceptable salt thereof, or the pharmaceutical composition thereof, and optionally in combination with a second therapeutic agent.

20. A method of treating elevated intraocular pressure, comprising administering to a subject in need of such treatment an effective amount of the compound of claim 10 or the pharmaceutically acceptable salt thereof.

* * * * *